US011097107B2

(12) United States Patent
Whiting et al.

(10) Patent No.: US 11,097,107 B2
(45) Date of Patent: Aug. 24, 2021

(54) EXTERNAL PACING DEVICE WITH DISCOMFORT MANAGEMENT

(71) Applicant: ZOLL MEDICAL CORPORATION, Chelmsford, MA (US)

(72) Inventors: Jason T. Whiting, Gibsonia, PA (US); Thomas E. Kaib, Irwin, PA (US); Rachel H. Carlson, Falls Creek, PA (US); Gregory R. Frank, Mt. Lebanon, PA (US); Gary A. Freeman, Waltham, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 125 days.

(21) Appl. No.: 16/407,844

(22) Filed: May 9, 2019

(65) Prior Publication Data

US 2019/0262608 A1    Aug. 29, 2019

Related U.S. Application Data

(63) Continuation of application No. 15/196,801, filed on Jun. 29, 2016, now Pat. No. 10,328,266, which is a
(Continued)

(51) Int. Cl.
*A61N 1/00* (2006.01)
*A61N 1/362* (2006.01)
(Continued)

(52) U.S. Cl.
CPC ............ *A61N 1/3625* (2013.01); *A61B 5/282* (2021.01); *A61B 5/361* (2021.01); *A61B 5/6831* (2013.01);
(Continued)

(58) Field of Classification Search
CPC ................ A61N 1/3625; A61N 1/0484; A61N 1/36014; A61N 1/046; A61N 1/3925;
(Continued)

(56) References Cited

U.S. PATENT DOCUMENTS 4,094,310 A    6/1978  McEachern et al.
4,393,874 A    7/1983  Nappholz et al.
(Continued)

FOREIGN PATENT DOCUMENTS

CN    1658927 A    8/2005
CN    102458572 A  5/2012
(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.
(Continued)

*Primary Examiner* — Scott M. Getzow
(74) *Attorney, Agent, or Firm* — Lando & Anastasi, LLP

(57) ABSTRACT

An external medical device includes a user interface; at least one therapy electrode configured to be disposed on a patient; and a processor operatively coupled to the at least one therapy electrode, the processor configured to cause a treatment manager to detect a cardiac condition of the patient; receive, via the user interface, discomfort information descriptive of the discomfort experienced by the patient; responsive to determining from the discomfort information that the patient is unconscious, execute at least one pacing routine, the at least one pacing routine being associated with the cardiac condition; and responsive to determining from
(Continued)

the discomfort information that the patient is conscious, adjust at least one characteristic of the at least one pacing routine.

13 Claims, 13 Drawing Sheets

Related U.S. Application Data continuation-in-part of application No. 15/079,294, filed on Mar. 24, 2016, now Pat. No. 9,675,804, which is a continuation of application No. 14/610,600, filed on Jan. 30, 2015, now Pat. No. 9,320,904, which is a continuation of application No. 13/907,523, filed on May 31, 2013, now Pat. No. 8,983,597.

(60) Provisional application No. 61/653,889, filed on May 31, 2012, provisional application No. 62/185,940, filed on Jun. 29, 2015.

(51) Int. Cl.
| | |
|---|---|
| *A61N 1/04* | (2006.01) |
| *A61N 1/36* | (2006.01) |
| *A61B 5/00* | (2006.01) |
| *A61N 1/39* | (2006.01) |
| *A61B 5/282* | (2021.01) |
| *A61B 5/361* | (2021.01) |

(52) U.S. Cl.
CPC ........... *A61N 1/046* (2013.01); *A61N 1/0484* (2013.01); *A61N 1/36014* (2013.01); *A61N 1/3621* (2013.01); *A61N 1/3925* (2013.01); *A61B 2562/17* (2017.08); *A61N 1/0456* (2013.01)

(58) Field of Classification Search
CPC ................ A61N 1/3621; A61N 1/0456; A61B 5/04085; A61B 5/046; A61B 5/6831; A61B 2562/17
See application file for complete search history.

(56) References Cited

U.S. PATENT DOCUMENTS

| | | | |
|---|---|---|---|
| 4,632,122 A | 12/1986 | Johansson et al. |
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,205,284 A | 4/1993 | Freeman |
| 5,282,843 A | 2/1994 | Freeman |
| 5,330,505 A | 7/1994 | Cohen |
| 5,348,008 A | 9/1994 | Bornn et al. |
| 5,357,696 A | 10/1994 | Gray et al. |
| 5,365,932 A | 11/1994 | Greenhut |
| 5,431,688 A | 7/1995 | Freeman |
| 5,662,689 A | 9/1997 | Elsberry et al. |
| 5,683,431 A | 11/1997 | Wang |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,766,225 A | 6/1998 | Kramm |
| 5,792,190 A | 8/1998 | Olson et al. |
| 5,797,967 A | 8/1998 | KenKnight |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,058,328 A | 5/2000 | Levine et al. |
| 6,065,154 A | 5/2000 | Hulings et al. |
| 6,097,987 A | 8/2000 | Milani |
| 6,148,233 A | 11/2000 | Owen et al. |
| 6,157,859 A | 12/2000 | Alt |
| 6,169,387 B1 | 1/2001 | Kaib |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,406,426 B1 | 6/2002 | Reuss et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,889,078 B2 | 5/2005 | Struble et al. |
| 6,889,079 B2 | 5/2005 | Bocek et al. |
| 6,908,437 B2 | 6/2005 | Bardy |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,130,690 B2 | 10/2006 | Rueter et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,392,081 B2 | 6/2008 | Wagner et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,831,303 B2 | 11/2010 | Rueter et al. |
| 7,974,689 B2 | 7/2011 | Volpe et al. |
| 7,979,122 B2 | 7/2011 | Favet et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,983,597 B2 | 3/2015 | Whiting et al. |
| 9,320,904 B2 | 4/2016 | Whiting et al. |
| 10,384,066 B2 | 8/2019 | Whiting et al. |
| 10,898,095 B2 | 1/2021 | Whiting et al. |
| 2002/0095188 A1 | 7/2002 | Mower |
| 2003/0004547 A1 | 1/2003 | Owen et al. |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0191404 A1 | 10/2003 | Klein |
| 2003/0195567 A1 | 10/2003 | Jayne et al. |
| 2003/0212311 A1 | 11/2003 | Nova et al. |
| 2004/0007970 A1 | 1/2004 | Ma et al. |
| 2004/0049233 A1 | 3/2004 | Edwards |
| 2004/0138713 A1 | 7/2004 | Stickney et al. |
| 2004/0172066 A1 | 9/2004 | Wagner et al. |
| 2004/0215239 A1 | 10/2004 | Favet et al. |
| 2005/0049515 A1 | 3/2005 | Misczynski et al. |
| 2005/0131465 A1 | 6/2005 | Freeman et al. |
| 2006/0036292 A1 | 2/2006 | Smith et al. |
| 2006/0085049 A1 | 4/2006 | Cory et al. |
| 2006/0178706 A1 | 8/2006 | Lisogurski et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0058884 A1 | 3/2008 | Matos |
| 2008/0086177 A1 | 4/2008 | Min et al. |
| 2008/0140139 A1 | 6/2008 | Heinrich et al. |
| 2008/0221397 A1 | 9/2008 | McMahon et al. |
| 2008/0249591 A1 | 10/2008 | Gaw et al. |

(56) References Cited

U.S. PATENT DOCUMENTS

| | | |
|---|---|---|
| 2008/0306562 A1 | 12/2008 | Donnelly et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0284486 A1 | 11/2009 | Albus |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0249860 A1 | 9/2010 | Shuros et al. |
| 2010/0268291 A1 | 10/2010 | Imran |
| 2010/0295674 A1 | 11/2010 | Hsieh et al. |
| 2010/0298899 A1* | 11/2010 | Donnelly .............. A61B 5/6805 607/6 |
| 2010/0312297 A1 | 12/2010 | Volpe et al. |
| 2010/0324621 A1 | 12/2010 | Libbus et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150244 A1 | 6/2012 | Freeman et al. |
| 2012/0158074 A1 | 6/2012 | Hall |
| 2012/0158075 A1 | 6/2012 | Kaib et al. |
| 2013/0338724 A1 | 12/2013 | Joo et al. |
| 2014/0364918 A1 | 12/2014 | Owen et al. |
| 2015/0297145 A1 | 10/2015 | Luna et al. |
| 2015/0335886 A1 | 11/2015 | Lu et al. |
| 2016/0175598 A1 | 6/2016 | Volpe et al. |
| 2016/0206886 A1 | 7/2016 | Whiting et al. |

FOREIGN PATENT DOCUMENTS

| | | |
|---|---|---|
| EP | 0295497 B1 | 9/1993 |
| EP | 0335356 B1 | 3/1996 |
| EP | 1455640 B1 | 1/2008 |
| EP | 1720446 B1 | 7/2010 |
| JP | 5115450 A | 5/1993 |
| JP | H10-127781 A | 5/1998 |
| JP | 2002-514107 A | 5/2002 |
| JP | 2002200059 A | 7/2002 |
| JP | 2002534233 A | 10/2002 |
| JP | 2004524074 A | 8/2004 |
| JP | 2004351122 A | 12/2004 |
| WO | 200002484 A1 | 1/2000 |
| WO | 2004054656 A1 | 7/2004 |
| WO | 2006050325 A2 | 5/2006 |
| WO | 20070057169 A1 | 5/2007 |
| WO | 2007077997 A1 | 7/2007 |
| WO | 2010025432 A1 | 3/2010 |

OTHER PUBLICATIONS

DeBock et al., "Captopril treatment of chronic heart failure in the very old," J. Gerontol. (1994) 49: M148-M152.

Internation Search Report and Written Opinion from corresponding PCT application PCT/US2013/043736, dated Sep. 4, 2013.

O'Keeffe et al., "Reproducability and responsiveness of quality of the assessment and six minute walk test in elderly heart failure patients," Heart (1998) 80: 377-382.

Reek et al. Clinical Efficacy of a Wearable Defibrillator Acutely Terminating Episodes of Ventricular Fibrillation Using Biphasic Shock.

* cited by examiner

EXTERNAL PACING DEVICE WITH DISCOMFORT MANAGEMENT

CROSS-REFERENCE TO RELATED APPLICATIONS

This application is a Continuation of U.S. patent application Ser. No. 15/196,801, titled "EXTERNAL PACING DEVICE WITH DISCOMFORT MANAGEMENT," filed on Jun. 29, 2016, which is a Continuation-in-Part of U.S. patent application Ser. No. 15/079,294, titled "MEDICAL MONITORING AND TREATMENT DEVICE WITH EXTERNAL PACING," filed on Mar. 24, 2016, now U.S. Pat. No. 9,675,804, which is a Continuation of U.S. patent application Ser. No. 14/610,600, titled "MEDICAL MONITORING AND TREATMENT DEVICE WITH EXTERNAL PACING," filed on Jan. 30, 2015, now U.S. Pat. No. 8,983,597, which is a Continuation of U.S. patent application Ser. No. 13/907,523, titled "MEDICAL MONITORING AND TREATMENT DEVICE WITH EXTERNAL PACING," filed on May 31, 2013, now U.S. Pat. No. 8,983,597, which claims priority under 35 U.S.C. § 119(e) to U.S. Provisional Application Ser. No. 61/653,889, titled "NONINVASIVE AMBULATORY MONITORING AND TREATMENT DEVICE WITH EXTERNAL PACING," filed on May 31, 2012, each of which is hereby incorporated herein by reference in its entirety. U.S. patent application Ser. No. 15/196,801 also claims the benefit of U.S. Provisional Patent Application Ser. No. 62/185,940, titled "EXTERNAL PACING DEVICE WITH DISCOMFORT MANAGEMENT," filed on Jun. 29, 2015, which is hereby incorporated by reference in its entirety.

BACKGROUND

Technical Field

The present disclosure is directed to noninvasive ambulatory medical devices, and more particularly, to a noninvasive medical monitoring and treatment device that is capable of externally pacing the heart of a patient wearing the device.

Discussion

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival.

To protect against cardiac arrest and other cardiac health ailments, some at-risk patients may use a wearable defibrillator, such as the LifeVest® wearable cardioverter defibrillator available from ZOLL® Medical Corporation of Chelmsford, Mass. To remain protected, the patient wears the device continuously or nearly continuously while going about their normal daily activities, while awake, and while asleep.

SUMMARY

Some aspects and embodiments of the present disclosure relate to controlling patient discomfort during administration of external pacing to the heart. For example, the systems and techniques described herein can be used in various medical monitoring and/or treatment devices. In some examples, the medical devices can be external or non-invasive, e.g., in contrast to internal or invasive devices, such as implantable medical devices. In some examples, a medical device as described herein can be bodily-attached, e.g., at least a portion of the device (other than its electrodes in the case of a defibrillator, cardioverter or pacer) is removably attached to the body of a patient, such as by mechanical coupling (for example, by a wrist strap, cervical collar, bicep ring), adhesion (for example, by an adhesive gel intermediary), suction, magnetism, fabric or other flexible material (for example, by straps or integration into a garment) or other body mounting features not limited by the aforementioned examples. In some examples, such coupling elements can hold the device in a substantially fixed position with respect to the body of the patient. In some examples, a medical device as described herein can be ambulatory, e.g., the device is capable of and designed for moving with the patient as the patient goes about his or her daily routine.

One example of a medical monitoring and treatment device suited for use with the systems and techniques described herein is the LifeVest® Wearable Cardioverter Defibrillator available from ZOLL® Medical Corporation of Chelmsford, Mass. A medical monitoring and treatment device can provide lifesaving defibrillation treatment to a patient suffering a treatable form of cardiac arrhythmia such as ventricular fibrillation (VF) or ventricular tachycardia (VT). Applicants have appreciated that such a medical monitoring and treatment device can be configured to perform a variety of different types of cardiac pacing to treat a wide variety of different cardiac arrhythmias, such as bradycardia, tachycardia, an irregular cardiac rhythm, and asystole (including asystole after a therapeutic shock). Applicants have further appreciated that, in other embodiments, a medical monitoring and treatment device can be configured to perform pacing to treat pulseless electrical activity. In accordance with an aspect of the present disclosure, the medical monitoring and treatment device can be configured to pace the heart of the patient at a fixed energy level (e.g., fixed current, fixed voltage, etc.) and pulse rate, to pace the heart of the patient on demand with a fixed energy level and an adjustable rate responsive to the detected intrinsic activity level of the patient's heart, or to pace the heart of the patient using capture management with an adjustable energy level and adjustable rate responsive to the detected intrinsic rate of the patient's heart and the detected response of the patient's heart to pacing, including both on a beat-by-beat basis and as analyzed over other various time intervals.

In some examples, the pacing parameters described above may be adjusted to lessen any discomfort experienced by the patient during pacing. In various examples, the patient can self-manage the administration of the pacing routine based on his or her own tolerance of the discomfort. In these examples, the medical monitoring and treatment device may begin pacing a patient using either default pacing parameters or baseline pacing parameters tailored to discomfort tolerances of the patient. The baseline pacing parameters may be configured by executing the medical monitoring and treatment device in a baseline mode during an initial fit of the device to the patient or by executing (or re-executing) the medical monitoring and treatment device in a baseline mode during subsequent operation of the device. It is appreciated that the pacing parameters may control, for example, the administration of pacing pulses, various characteristics of the pacing pulses, the administration of TENS pulses, and/or various characteristics of the TENS pulses.

In one aspect of the present invention, an external medical device is provided comprising at least one therapy electrode configured to be disposed on a patient, and a treatment manager, coupled to the at least one therapy electrode, configured to execute a baseline process to determine at least one of a range of values for a discomfort parameter corresponding to at least one pacing routine and a patient discomfort threshold value corresponding to the at least one pacing routine, detect a cardiac condition of the patient, execute the at least one pacing routine, the at least one pacing routine being associated with the cardiac condition, monitor the discomfort parameter associated with the patient during execution of the at least one pacing routine, determine whether the discomfort parameter transgresses the at least one of the range of values and the patient discomfort threshold value, and adjust at least one characteristic of the at least one pacing routine in response to determining that the discomfort parameter transgresses the at least one of the range of values and the patient discomfort threshold value. In one embodiment, the device further comprises a user interface for receiving discomfort information regarding the patient in connection with the at least one pacing routine. In one embodiment, the discomfort parameter is based on at least one of the discomfort information received from a user via the user interface and information automatically detected by at least one sensor distinct from the user interface. In another embodiment, the user interface comprises at least one of a touch screen, a button, a microphone for receiving audible commands, a strain gauge, a force sensor, a piezoelectric transducer, and a rotating spring-loaded dial.

In an alternative embodiment, the treatment manager is configured to receive the discomfort information descriptive of the discomfort parameter with reference to an amount of pressure exerted by the user on an element of the user interface. In one embodiment, the treatment manager is configured to determine a present value of the discomfort parameter during execution of the at least one pacing routine based on at least one of an amount of pressure detected by the user interface and a duration of time the element of the user interface remains actuated. In one embodiment, the element of the user interface is at least one of a quartz sensor, a ceramic force sensor, and a piezoelectric transducer. In another embodiment, the user interface comprises a force sensor configured to detect a force applied by the user squeezing at least one surface of the force sensor. In yet another embodiment, the at least one sensor includes at least one of a motion sensor, an audio sensor, a physiological sensor, an electrode, an accelerometer, and a blood pressure sensor.

In one embodiment, the treatment manager is configured to receive the discomfort information regarding the patient responsive to selection of an element of the user interface. In one embodiment, the user interface displays a discomfort scale and the element includes a selectable point on the discomfort scale. In one embodiment, the discomfort scale is at least one of numeric and image-based. In one embodiment, the user interface includes a touch screen configured to display a plurality of selectable points on the discomfort scale. In another embodiment, the selection includes at least one of a touch and an utterance. In an alternative embodiment, the utterance includes at least one predefined word.

In another embodiment, the treatment manager is further configured to detect, via a touch detector, a touch having a duration, and determine whether the discomfort parameter transgresses the patient discomfort threshold value based on the duration. In one embodiment, the treatment manager is further configured to adjust at least one characteristic of the at least one pacing routine in response to determining that a value of the discomfort parameter is equal to or transgresses the patient discomfort threshold value. In one embodiment, the at least one characteristic of the at least one pacing routine includes at least one of an amplitude of pacing pulses, a width of the pacing pulses, a rate of the pacing pulses, a waveform of the pacing pulses, a period of the pacing pulses, a duty cycle of the pacing pulses, and a ramp time constant of the pacing pulses. In another embodiment, the cardiac condition comprises at least one of bradycardia, tachycardia, asystole, pulseless electrical activity, and erratic heart rate.

In one embodiment, the at least one pacing routine comprises at least one of fixed rate pacing, fixed energy pacing, adjustable rate pacing, and capture management pacing. In one embodiment, the discomfort parameter is indicative of a level of discomfort experienced by the patient during the at least one pacing routine. In one embodiment, the treatment manager is configured to execute the baseline process during an initial fitting of the external medical device to the patient. In another embodiment, the treatment manager is further configured to optimize at least one characteristic of the at least one pacing routine in response to the determination that the discomfort parameter transgresses the at least one of the range of values and the patient discomfort value.

In an alternative embodiment, the treatment manager is configured to optimize the at least one characteristic along a scale selected from at least one of a linear scale, a logarithmic scale, and an exponential scale. In one embodiment, the treatment manager is configured to optimize the at least one characteristic at least in part by executing a regression analysis using historical values of the at least one characteristic. In one embodiment, the treatment manager is further configured to adjust the patient discomfort threshold value based on the patient's state of consciousness. In another embodiment, the device further comprises a transcutaneous electrical nerve stimulation unit configured to provide background stimulation to the patient during execution of the at least one pacing routine.

In one embodiment, executing the baseline process further comprises setting at least one characteristic of the at least one pacing routine to an appropriate level based on a physiological condition of the patient. In one embodiment, the appropriate level is determined based on typical impedance values for an adult or child. In another embodiment, executing the baseline process further comprises setting at least one characteristic of the at least one pacing routine with reference to pacing parameter baselines associated with multiple patients.

In another aspect of the present invention, a method of controlling patient discomfort during pacing by an external medical device is provided comprising determining, during a baseline process, at least one of a range of values for a discomfort parameter corresponding to at least one pacing routine of the external medical device and a patient discomfort threshold value corresponding to the at least one pacing routine, detecting a cardiac condition of the patient, the cardiac condition being associated with the at least one pacing routine, executing the at least one pacing routine, monitoring the discomfort parameter of the patient during execution of the at least one pacing routine, and adjusting, responsive to the discomfort parameter transgressing at least one of the range of values and the patient discomfort threshold value, at least one characteristic of the at least one pacing routine. In one embodiment, the method further comprises receiving, via a user interface, discomfort information regarding the patient in connection with the at least one pacing routine. In one embodiment, the discomfort parameter is based on at least one of the discomfort information received from a user via the user interface and information automatically detected by at least one sensor distinct from the user interface. In another embodiment, the method further comprises receiving the discomfort information from a user selection of an element of the user interface.

In one embodiment, the user interface comprises a touch sensor, the method further comprising detecting, via the touch sensor, a touch having a duration, and determining whether the discomfort parameter is equal to or transgresses the patient discomfort threshold value with reference to the duration. In another embodiment, executing the baseline process further comprises setting at least one characteristic of the at least one pacing routine to an appropriate level based on at least one of a physiological condition of the patient, typical impedance values for an adult or child, and pacing parameter baselines associated with multiple patients.

In an alternative aspect of the present invention, a bodily-attached ambulatory medical device is provided comprising at least one therapy electrode configured to be disposed on a patient, and a treatment manager, coupled to the at least one therapy electrode, configured to execute a baseline process to determine at least one of a range of values for a discomfort parameter corresponding to at least one pacing routine and a patient discomfort threshold value corresponding to the at least one pacing routine, detect a cardiac condition of the patient, and execute the at least one pacing routine, the at least one pacing routine being associated with the cardiac condition and having at least one characteristic configured for the patient's tolerance for discomfort based on the at least one of the range of values for the discomfort parameter and the patient discomfort threshold value.

Still other aspects, embodiments, and advantages of these exemplary aspects and embodiments are discussed in detail below. Moreover, it is to be understood that both the foregoing information and the following detailed description are merely illustrative examples of various aspects and embodiments of the present disclosure, and are intended to provide an overview or framework for understanding the nature and character of the claimed aspects and embodiments. Any embodiment or example disclosed herein may be combined with any other embodiment or example in any manner consistent with at least one of the aspects disclosed herein, and references to "an embodiment," "an example," "some embodiments," "some examples," "an alternate embodiment," "an alternate example," "various embodiments," "various examples," "one embodiment," "one example," "at least one embodiment," "at least one example," "this and other embodiments," "this and other examples," or the like are not necessarily mutually exclusive and are intended to indicate that a particular feature, structure, or characteristic described in connection with the embodiment may be included in at least one embodiment. The appearance of such terms herein is not necessarily all referring to the same embodiment.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Figure 1:
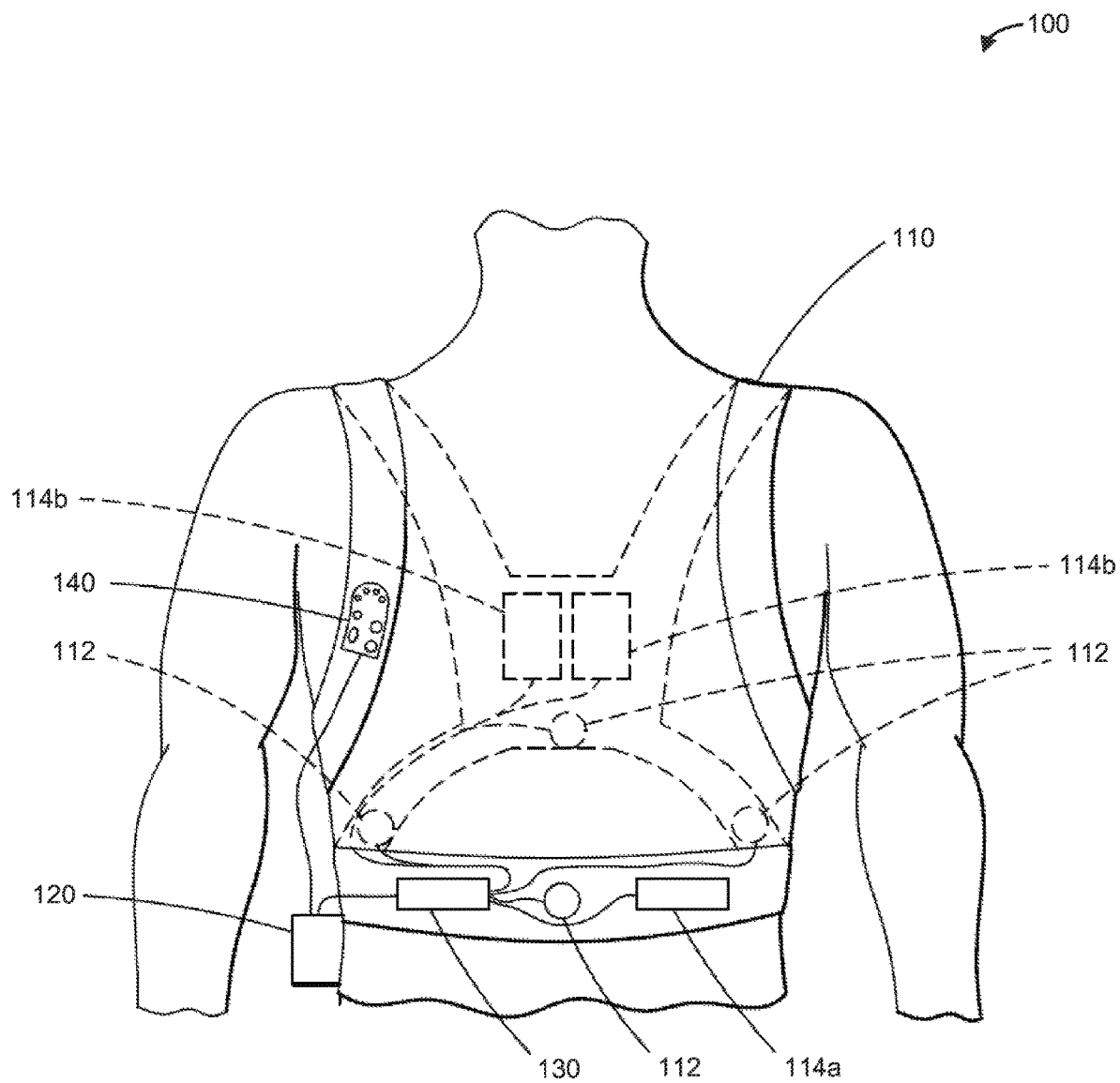
FIG. 1 is an illustration of one example of a wearable medical device.

Medical monitoring and treatment devices in accord with various examples disclosed herein are configured to monitor and control discomfort experienced by a patient while administering therapy to the patient. For instance, in at least one example, a medical device is configured to provide pacing therapy to a patient and to control parameters of a pacing routine to decrease the level of discomfort experienced by the patient. In some examples, the medical device is configured to allow the patient to self-manage execution of the pacing routine (e.g., dynamically control one or more parameters of the pacing routine) based on his or her own tolerance of the discomfort in real time or near real time.

In some examples, the medical device is configured to receive input descriptive of a level of discomfort being experienced by the patient, calculate a value quantifying of the level of discomfort being experienced by the patient, determine whether the value is equal to or transgresses a discomfort threshold value, and, if so, adjust a parameter of the pacing routine to decrease the level of discomfort.

Medical devices disclosed herein may be invasive or non-invasive. For example, medical devices disclosed herein may be monitoring devices (e.g., configured to monitor a cardiac signal of a patient) with or without an associated treatment component. For example, a non-invasive medical device suited for use with the systems and techniques as disclosed herein can include an automated external defibrillator (AED). Such AEDs are capable of monitoring cardiac rhythms, determining when a defibrillating shock is needed, and administering the shock either automatically or under the control of a trained rescuer (e.g., an EMT or other medically trained personnel). The AED may also be configured to provide cardiopulmonary resuscitation (CPR) counseling. Such AEDs are available from ZOLL® Medical Corporation of Chelmsford, Mass.

The devices as described herein may be capable of continuously, substantially continuously, long-term and/or extended use or wear by, or attachment or connection to a patient.

For example, devices as described herein may be capable of being used or worn by, or attached or connected to a patient, without substantial interruption for a predetermined period of time. In some examples, such devices may be capable of being used or worn by, or attached or connected to a patient for example, up to hours or beyond (e.g., weeks, months, or even years).

In some implementations, such devices may be removed for a period of time before use, wear, attachment, or connection to the patient is resumed, e.g., to change batteries, to change the garment, and/or to take a shower, without departing from the scope of the examples described herein.

The devices as described herein may be capable of continuously, substantially continuously, long-term and/or extended monitoring of a patient.

For example, devices as described herein may be capable of providing cardiac monitoring without substantial interruption for a predetermined period of time. In some examples, such devices may be capable of continuously or substantially continuously monitoring a patient for cardiac-related information (e.g., ECG information, including arrhythmia information, heart sounds, etc.) and/or non-cardiac information (e.g., blood oxygen, the patient's temperature, glucose levels, and/or lung sounds), for example, up to hours or beyond (e.g., weeks, months, or even years).

In some implementations, such devices may be powered down for a period of time before monitoring is resumed, e.g., to change batteries, to change the garment, and/or to take a shower, without departing from the scope of the examples described herein.

In some instances, the devices may carry out its monitoring in periodic or aperiodic time intervals or times. For example, the monitoring during intervals or times can be triggered by a user action or another event. For example, one or more durations between the periodic or aperiodic intervals or times can be user-configurable.

In various implementations, the devices may be operated on battery power for a duration of the device's use after which the batteries may be replaced and/or recharged.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

In implementations where example numerical values are provided (e.g., as a predetermined numerical value), it should be understood that such values can be set through one or more user-configurable parameters. For example, the example numerical value can be provided as a default value, and a technician or a caregiver (such as a nurse or physician) can modify the values in accordance with the principles described herein through a user interface.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Example Wearable Medical Device

In one example, the medical monitoring and treatment device is a wearable medical device that includes a garment (e.g., a vest or belt) that is worn by the patient. The wearable medical device monitors the patient's electrocardiogram (ECG) with sensing electrodes, detects life-threatening arrhythmias, and delivers pacing pulses or a cardioverting or defibrillating shock through therapy pads if treatment is necessary. In examples, the wearable medical device is configured to monitor the patient and the patient's environment to quantify a level of discomfort being experienced by the patient and optimize the effectiveness of a pacing routine while preventing the level of discomfort of the patient from exceeding a threshold.

FIG. 1 illustrates an example wearable medical device for use with the systems and techniques described herein. As shown, the wearable medical device 100 includes a harness 110 having a pair of shoulder straps and a belt that is worn about the torso of a patient. The harness 110 is typically made from a material, such as cotton, nylon, spandex, or Antron® that is breathable, and unlikely to cause skin irritation, even when worn for prolonged periods of time. The wearable medical device 100 includes a plurality of ECG sensing electrodes 112 that are attached to the harness 110 at various positions about the patient's body and electrically coupled (wirelessly or by a wired connection) to a sensor interface of the medical device controller 120 via a connection pod 130. The plurality of ECG sensing electrodes 112, which may be dry-sensing capacitance electrodes, are coupled to the medical device controller 120 to monitor the cardiac function of the patient and generally include a front-back (FB) pair of ECG sensing electrodes and a side-side (SS) pair of ECG sensing electrodes. Additional ECG sensing electrodes may be provided, and the plurality of ECG sensing electrodes 112 may be disposed at varying locations about the patient's body. The plurality of ECG sensing electrodes 112 may incorporate any electrode system, including conventional stick-on adhesive electrodes, dry-sensing capacitive ECG electrodes, radio transparent electrodes, segmented electrodes, or one or more long term wear electrodes that are configured to be continuously or substantially continuously worn by a patient for extended periods (e.g., 3 or more days). One example of such a long term wear electrode is described in U.S. Patent Application Publication No. US2013/0325096 (hereinafter the "'096 publication"), titled "LONG TERM WEAR MULTIFUNCTION BIOMEDICAL ELECTRODE," published Dec. 5, 2013, which is hereby incorporated herein by reference in its entirety.

The wearable medical device disclosed herein may incorporate sundry materials arranged in a variety of configurations to maintain a proper fit with the patient's body. For example, some embodiments include a garment as described in U.S. Patent Application Publication No. US2012/0283794, titled "PATIENT-WORN ENERGY DELIVERY APPARATUS AND TECHNIQUES FOR SIZING SAME," published Nov. 8, 2012, which is hereby incorporated herein by reference in its entirety. In one example, the garment includes one or more strain gauges configured to generate signals when pressed upon by the patient or when the patient twists away from a source of discomfort. In this example, the amount of deformation indicated by the signals is quantified by the wearable medical device for use in managing the discomforted experience by the patient. Thus embodiments are not limited to the configuration and materials described above with reference to FIG. 1.

The wearable medical device 100 also includes a plurality of therapy electrodes 114*a* and 114*b* that are electrically coupled to the medical device controller 120 via the connection pod 130 and which are configured to deliver one or more therapeutic pacing pulses or defibrillating shocks to the body of the patient, if it is determined that such treatment is warranted. As shown, the therapy electrodes 114 include a first therapy electrode 114*a* that is disposed on the front of the patient's torso and a second therapy electrode 114*b* that is disposed on the back of the patient's torso. The second therapy electrode 114*b* includes a pair of therapy electrodes that are electrically coupled together and act as the second therapy electrode 114*b*. The use of two therapy electrodes 114*a*, 114*b* permits a pacing pulse or other therapeutic shock having any of a variety of waveforms to be delivered to the body of the patient. The plurality of therapy electrodes 114 may incorporate any electrode system, including conventional stick-on adhesive electrodes, segmented electrodes, integrated electrodes (e.g., including electrode patches or assemblies integrating both sensing and therapy electrodes), or one or more long term wear electrodes that are configured to be continuously or substantially continuously worn by a patient for extended periods (e.g., 3 or more days). Example electrodes are described in '096 publication, which is hereby incorporated herein by reference in its entirety.

One of these waveforms is a biphasic waveform in which a first of the two therapy electrodes can deliver a first phase of the biphasic pulse or shock with the other therapy electrode acting as a return, and the other therapy electrode can deliver the second phase of the biphasic pulse or shock with the first therapy electrode acting as the return. Other waveforms may be generated by this arrangement and several are described further below.

In some examples, the wearable medical device includes one or more reservoirs of conductive gel. In these examples, the wearable medical device is configured to, prior to delivering the pulses or shock, deploy the conductive gel from the reservoir to reduce an impedance encountered by the therapy electrodes during the delivery of the pacing pulses or a defibrillating shock.

The connection pod 130 electrically couples the plurality of ECG sensing electrodes 112 and the plurality of therapy electrodes 114 to the medical device controller 120, and may include electronic circuitry. For example, in one implementation the connection pod 130 includes signal acquisition circuitry, such as a plurality of differential amplifiers to receive ECG signals from different electrodes of the plurality of ECG sensing electrodes 112 and to provide a differential ECG signal to the medical device controller 120 based on the difference there between. The connection pod 130 may also include other electronic circuitry, such as a motion sensor or accelerometer through which patient activity may be monitored.

In some embodiments, both the first therapy electrode 114*a* and the second therapy electrode 114*b* are disposed on the front of the patient's torso. For example, the first therapy electrode 114*a* may be located external to the apex of the heart and the second therapy electrode 114*b* may be located along the parasternal line. Thus embodiments are not limited to a particular arrangement of therapy electrodes.

In some embodiments, the plurality of ECG sensing electrodes 112 are positioned and paired such that artifacts generated from electrical activity are decreased. In other embodiments, the electronic circuitry included in the medical device controller 120 may equalize artifacts measured at electrodes by changing a gain or impedance. Other techniques of decreasing or preventing artifacts within measured electrical activity that may be used in conjunction with the embodiments disclosed herein are explained in U.S. Pat. No. 8,185,199, titled "MONITORING PHYSIOLOGICAL SIGNALS DURING EXTERNAL ELECTRICAL STIMULATION," issued May 22, 2012, which is hereby incorporated herein by reference in its entirety.

Although not shown, the wearable medical device 100 may include additional sensors, other than the ECG sensing electrodes 112, capable of monitoring the physiological condition or activity of the patient. For example, sensors capable of measuring blood pressure, muscular contraction, perspiration, heart rate, heart sounds, thoracic impedance, pulse oxygen level, respiration rate, and the activity level of the patient may also be provided.

As shown in FIG. 1, the wearable medical device 100 may include a user interface pod 140 that is electrically coupled to, integrated in, and/or integrated with, the user interface of the medical device controller 120. The user interface pod 140 can be attached to the patient's clothing or to the harness 110, for example, via a clip (not shown) that is attached to a portion of the interface pod 140. Alternatively, the user interface pod 140 may simply be held in a person's hand. For example, such a user interface pod 140 can be a smartwatch or a smartphone. In some examples, the user interface pod 140 may communicate wirelessly with the user interface of the medical device controller 120, for example, using a Bluetooth®, Wireless USB, ZigBee, Wireless Ethernet, GSM, or other type of communication interface.

The user interface pod 140 includes a number of buttons by which the patient, or a bystander can communicate with the medical device controller 120, and a speaker by which the medical device controller 120 may communicate with the patient or the bystander. For example, where the medical device controller 120 determines that the patient is experiencing cardiac arrhythmia, the medical device controller 120 may issue an audible alarm via a speaker on the medical device controller 120 or the user interface pod 140 alerting the patient and any bystanders to the patient's medical condition. Examples of notifications issued by the medical device controller 120 are described in U.S. Patent Application Publication No. US2012/0293323, titled "SYSTEM AND METHOD FOR ADAPTING ALARMS IN A WEARABLE MEDICAL DEVICE," published Nov. 22, 2012, which is hereby incorporated herein by reference in its entirety.

In some examples, the medical device controller 120 may instruct the patient to press and hold one or more buttons on the user interface of the medical device controller 120 or on the user interface pod 140 to indicate that the patient is conscious, thereby signaling the medical device controller 120 to withhold the delivery of one or more therapeutic pacing pulses or defibrillating shocks. If the patient does not respond, the device may determine that the patient is unconscious, and proceed with the treatment sequence, culminating in delivery of defibrillating shocks or one or more pacing pulses with parameters set to maximum values to the body of the patient.

In some examples, as described in detail below, the medical device controller 120 may (depending on a type of user interface element, e.g., one or more buttons on a user interface) instruct the patient to press and hold the one or more buttons on the user interface with a force proportional to the intensity of discomfort being experienced by the patient during execution of a pacing routine, thereby signaling the medical device controller 120 to adjust parameters of the pacing routine to decrease the intensity of the discomfort. If the patient does not respond, the device may determine that the patient is unconscious, and proceed with the treatment sequence, culminating in the delivery of one or more pacing pulses to the body of the patient. For example, the medical device may administer a pacing routine with values for the pacing parameters as an upper bound of a range of values (e.g., to maximize efficacy) as described below. As the patient recovers consciousness, the patient may (depending on a type of user interface element), in real time or near real time, increase the force exerted on the one or more buttons, thereby signaling the medical device to adjust the parameters of the pacing routine. The medical device may, in response to receiving the signal, decrease the intensity of the discomfort by, for example, decreasing the values of the pacing parameters (which may result in a corresponding decrease in efficacy). If the patient were to once again lose consciousness or feel faint, e.g., as a result of bradycardia, the patient may not be able to continue to exert a same level of force on the one or more buttons. Correspondingly, the medical device can dynamically adjust the values of the pacing parameters to increase the efficacy of the pacing routine.

In some situations where the patient fails to provide voluntary feedback regarding his/her level of discomfort, a threshold value can be set for a discomfort parameter as outlined below. When the sensed level of discomfort is equal to or transgresses the threshold, the medical device can adjust the values of the pacing parameters to lower the intensity of the pacing routine. In some examples, the medical device can check for capture before, after, or substantially simultaneous with adjusting the values of the pacing parameters as described in further detail below.

In some implementations, one or more response buttons and/or user interface elements for managing discomfort during a pacing routine may be different from one or more response buttons for establishing user responsiveness prior to delivering a defibrillating shock.

Figure 2A:
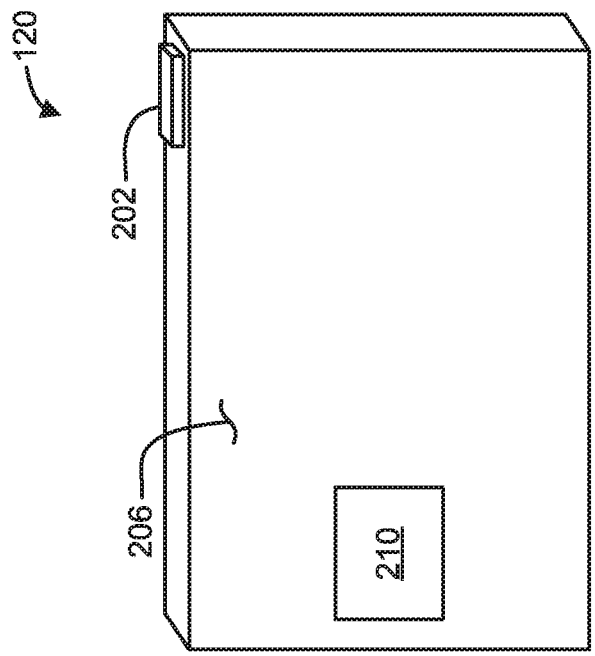
FIGS. 2A-2B are illustrations of one example of a medical device controller for an ambulatory medical device.
Figure 2B:
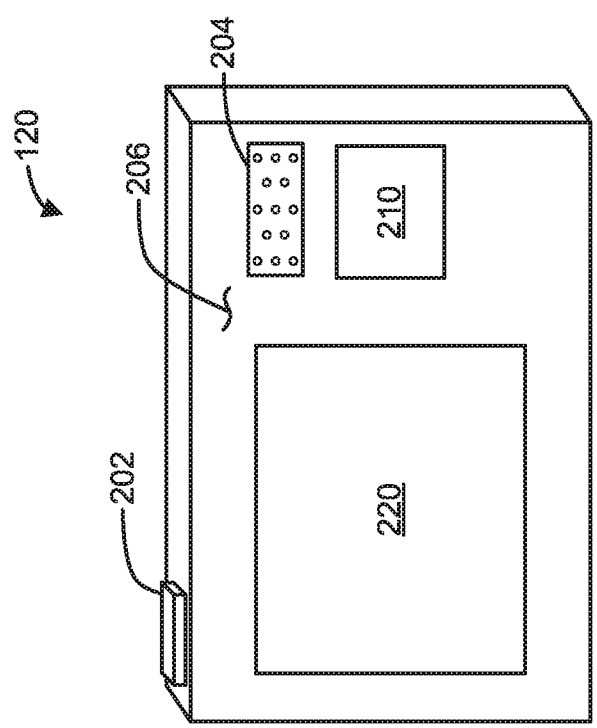

In another example, the functionality of the user interface pod 140 is integrated into the housing of the medical device controller 120. FIGS. 2A-2B illustrate such an example of the medical device controller 120. The medical device controller 120 includes two response buttons 210 on opposing sides of a housing 206 of the medical device controller 120. As shown in FIGS. 2A-2B, the response buttons 210 are recessed to reduce the likelihood of accidental activation (e.g., a patient falling on the response button). The medical device controller 120 also includes, in this example, a display screen 220 and a speaker 204 to enable the communication of audible and visual stimuli to the patient. It is appreciated that the response buttons 210 do not have to be placed on opposing sides of the housing as illustrated in FIGS. 2A-2B. The response buttons 210, for example, may be located adjacent to each other in the housing the ambulatory medical device controller. The adjacent placement of the response buttons may make it easier for individuals with smaller hands or less dexterity to engage the response buttons. The medical device controller 120 may further include a connector 202 to removably connect sensing electrodes (e.g., ECG sensing electrodes 112) and/or therapy electrodes (e.g., therapy electrodes 114a and 114b) to the medical device controller 120.

Another example wearable medical device includes an ambulatory external defibrillator described in FIG. 1 of U.S. Pat. No. 8,904,214, titled "SYSTEM AND METHOD FOR CONSERVING POWER IN A MEDICAL DEVICE," issued Dec. 2, 2014 (hereinafter the "'214 patent"), which is hereby incorporated herein by reference in its entirety. In at least one example, the ambulatory defibrillator 100 illustrated in FIG. 1 of the '214 patent may employ the medical device controller 120, as disclosed in the present application, as a substitute for the medical device controller 200 described in the '214 patent. In such an example, the ECG Electrodes and Therapy Pads illustrated in FIG. 1 of the '214 patent may be logically and physically coupled to the medical device controller 120. While some of the examples disclosed herein are directed to wearable medical devices, the systems and methods disclosed herein may be readily applied to other medical devices including, for example, an Automated External Defibrillator (AED).

In some implementations, the medical device as described herein can be a hospital-based wearable defibrillator and/or pacing device. For example, such a hospital-based device can include a defibrillator and/or pacing device configured for continuous or substantially continuous use, wear, connection, attachment, or monitoring to/of a patient in a hospital environment. The hospital-based device can include a plurality of therapy and sensing electrodes that are attached to the patient's skin. In some examples, the electrodes are disposable adhesive electrodes. In some implementations, the electrodes are affixed to an electrode assembly (a patch), which can then be adhesively attached to the patient's skin. The electrodes can be attached to the patient's skin at particular locations as prescribed by a trained professional.

In operation, the hospital-based device can include a monitor configured to operate in a manner that is different from that of the monitor of wearable defibrillator described above with respect to FIG. 1. For example, an interface, prompts, and communication performed by the hospital-based device can be configured for and/or directed to a user other than the patient, e.g., a caregiver such as a nurse or a patient service representative. For example, a caregiver can program the device and/or set the device up for use by the patient. The interface, prompts, and communication can be directed to the patient in scenarios such as when a response is required to let the device know whether or not the patient is conscious, which can be used in deciding when to shock the patient, and when a patient is given an alert to call the caregiver.

Example Medical Device Controller

Figure 3:
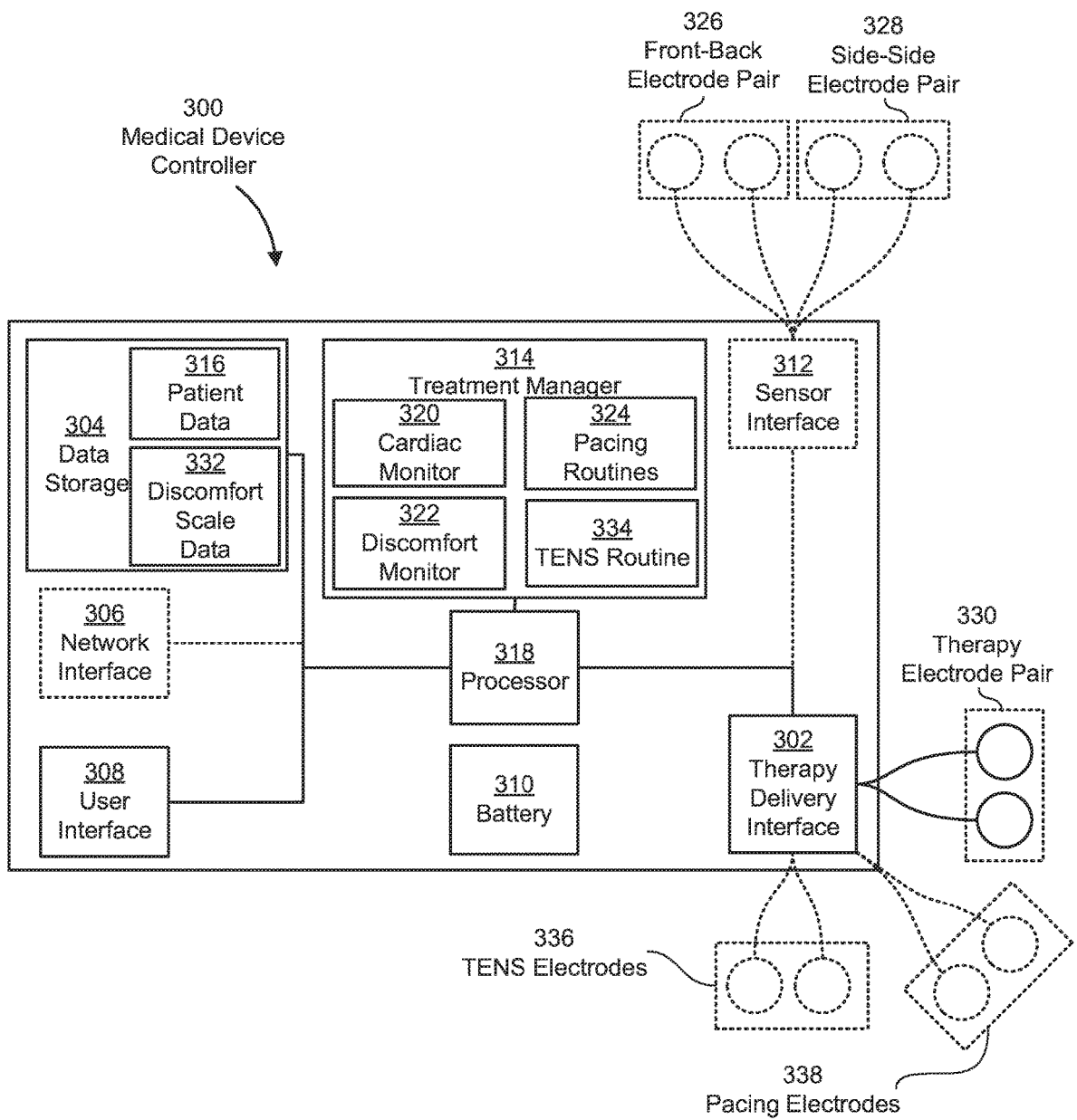
FIG. 3 is a functional schematic of one example of a medical device controller.

FIG. 3 illustrates a medical device controller 300 that is configured to monitor the cardiac activity of a patient and/or provide pacing or other therapy to the patient as needed. The medical device controller 300 may, for example, be configured for use in a wearable medical device (e.g., medical device controller 120). The medical device controller 300 has a variety of potential applications and is well suited to devices that notify external entities of one or more events of interest (e.g., cardiac events). Examples of medical devices to which the medical device controller 300 is well suited include critical care medical devices, such as a wearable ambulatory external defibrillator, an AED, pacing devices, or a mechanical chest compression device, such as the Autopulse® system from ZOLL® Medical Corporation of Chelmsford, Mass.

As shown in FIG. 3, the medical device controller 300 includes a processor 318, a sensor interface 312, a treatment manager 314, a therapy delivery interface 302, data storage 304, a communication network interface 306, a user interface 308, and a battery 310. The data storage 304 includes patient data 316 and discomfort scale data 332. The treatment manager 314 includes a cardiac monitor 320, a discomfort monitor 322, one or more pacing routines 324, and a transcutaneous electrical nerve stimulation (TENS) routine 334. Both the sensor interface 312 and the network interface 306 are illustrated using dashed lines to indicate they are optional components in at least some examples. The sensor interface 312, as illustrated, is coupled to electrodes including a front-back (FB) electrode pair 326 and a side-side (SS) electrode pair 328.

The therapy delivery interface 302, as illustrated, can be coupled to one or more therapy electrodes, e.g., therapy electrode pair 330. The therapy delivery interface 302 may be optionally coupled to one or more TENS electrodes (e.g., TENS electrodes 336) and/or one or more pacing electrodes (e.g., pacing electrodes 338). For example, TENS electrodes 336 may include a TENS electrode pair, and pacing electrodes 338 may include a pacing electrode pair. It is appreciated that the electrode configuration and/or the number of electrodes may be changed to best suit the particular application. For example, the therapy delivery interface 302 may be coupled to the therapy electrode pair 330 and provide any combination of defibrillation pulses, pacing pulses, and TENS pulses to the patient via the therapy electrode pair 330. In some implementations, the therapy delivery interface 302 may be coupled to separate pacing electrodes 338 for providing pacing pulses in addition to the therapy electrode pair 330 for providing defibrillation pulses. Accordingly, the TENS pulses may be provided to the patient via either the pacing electrodes 338 and/or the therapy electrode pair 330 under control of a treatment protocol as described herein. As such, the therapy delivery interface 302 may be coupled to any combination of the therapy electrode pair 330, the TENS electrodes 336, and pacing electrodes 338 to provide treatment to the patient.

In some examples, the therapy delivery interface 302 is coupled to at least the therapy electrode pair 330 and the pacing electrodes 338. Employing the therapy electrode pair 330 to provide defibrillation pulses and separate pacing electrodes 338 to provide pacing pulses may be advantageous, for example, where different electrode configurations enable different gels to be deployed for pacing and defibrillation. For example, the therapy electrode pair 330 may be configured to deploy a gel with a low impedance and the pacing electrodes 338 may be configured to deploy a gel with a higher impedance. In these examples, the therapy delivery interface 302 may delivery defibrillation pulses via the therapy electrode pair 330 and deliver pacing and/or TENS pulses via the pacing electrodes 338 and/or another electrode pair (e.g., TENS electrodes 336).

For example, the therapy electrodes (or, in some implementations, pacing electrodes) may deploy a high impedance gel (e.g., 500 ohms) to decrease external skin pain during pacing routines as described herein. For example, the therapy electrodes may also be configured to dispense a low impedance gel (e.g., 1 ohm) should defibrillation be required before or after pacing.

In some examples, the battery 310 is a rechargeable battery that provides electrical power to other components within the medical device. The particular capacity and type of battery (e.g., lithium ion, nickel-cadmium, or nickel-metal hydride) employed may vary based on the desired runtime between charges of the medical device and the power consumption of the components. For example, the battery 310 may be selected to provide a minimum runtime between charges of 44 hours. In this example, a suitable battery may include a 3 cell 4200 mAh lithium ion battery pack. It is appreciated that various mechanisms may be employed to removably secure the battery 310 to the medical device controller 300 including, for example, a latching mechanism.

According to the example illustrated in FIG. 3, the processor 318 is coupled to the sensor interface 312, the therapy delivery interface 302, the data storage 304, the network interface 306, and the user interface 308. The processor 318 performs a series of instructions that result in manipulated data which are stored in and retrieved from the data storage 304. According to a variety of examples, the processor 318 is a commercially available processor such as a processor manufactured by Texas Instruments, Intel, AMD, Sun, IBM, Motorola, Freescale, and ARM Holdings. However, the processor 318 may be any type of processor, multiprocessor or controller, whether commercially available or specially manufactured. For instance, according to one example, the processor 318 may include a power conserving processor arrangement such as described in the '214 patent. In another example, the processor 318 is an Intel® PXA270.

In addition, in some examples, the processor 318 may be configured to execute a conventional operating system. The operating system may provide platform services to application software, such as some examples of the treatment manager 314 which are discussed further below. These platform services may include inter-process and network communication, file system management and standard database manipulation. One or more of many operating systems may be used, and examples are not limited to any particular operating system or operating system characteristic. For instance, operating systems can include a Windows based operating system, OSX, or other operating systems. For instance, in some examples, the processor 318 may be configured to execute a real time operating system (RTOS), such as RTLinux, or a non-real time operating system, such as BSD or GNU/Linux.

In some examples, the treatment manager 314 is configured to monitor the cardiac activity of the patient, identify cardiac events experienced by the patient, treat identified cardiac events, and manage discomfort experienced by patients during treatment. In these examples, the cardiac monitor 320 is configured to process data descriptive of cardiac function to identify cardiac events. The one or more pacing routines 324 are configured to apply one or more pacing pulses via the therapy electrode pair 330 to the patient to treat arrhythmias, such as bradycardia. For example, the wearable medical device can be configured to treat a patient experiencing bradycardia when the patient's heart rate is about 40 beats per minute or less.

In some examples, prior to and during the execution of one or more pacing routines, the discomfort monitor 322 can request that the user interface 308 instruct the patient to press and hold one or more buttons on the user interface with a force proportional to the intensity of discomfort being experienced by the patient during execution of the one or more pacing routines. In this manner, the discomfort monitor 322 can adjust the parameters of the pacing routine to increase or decrease the intensity of the one or more pacing routines based on the patient's comfort level and/or efficacy of the routines. For example, if the patient does not respond, the discomfort monitor 322 may determine that the patient is unconscious, and proceed with the treatment sequence, culminating in the delivery of one or more pacing pulses to the body of the patient. For example, the medical device may administer a pacing routine with values for the pacing parameters as an upper bound of a range of values (e.g., to maximize efficacy) as described below. As the patient recovers consciousness, the patient may (depending on a type of user interface element), in real time or near real time, increase the force exerted on the one or more buttons of the user interface 308, thereby signaling the medical device to adjust the parameters of the pacing routine. The discomfort monitor 322 may, in response to receiving the signal, decrease the intensity of the discomfort by, for example, decreasing the values of the pacing parameters (with a corresponding decrease in efficacy).

In some implementations, the discomfort monitor 322 is configured to receive input descriptive of patient discomfort, quantify a level of discomfort being experienced by the patient, compare the quantified level of discomfort to a discomfort threshold value, and adjust parameters of the active pacing routine to decrease the level of discomfort being experienced by the patient. One of the parameter adjustments that may be executed by the discomfort monitor 322 is execution of the TENS routine 334. The TENS routine 334 is configured to apply one or more TENS pulses to a patient via, for example, one or more TENS electrodes 336. It is appreciated that the TENS pulses may be applied by other electrodes including, for example, the therapy electrode pair 330 and/or one or more pacing electrodes 338. These TENS pulses may serve to distract the patient so that the level of discomfort experienced by the patient is lessened. In some examples, the TENS pulses are applied in intervals between pacing pulses. Additional description regarding the use of TENS pulses in conjunction with external pacing is provided in U.S. Pat. No. 5,205,284, titled "METHOD AND APPARATUS FOR TRANSCUTANEOUS ELECTRICAL CARDIAC PACING WITH BACKGROUND STIMULATION" and issued on Apr. 27, 1993, which is hereby incorporated herein by reference in its entirety.

Processes executed by the treatment manager 314 and its constituent components (i.e., the cardiac monitor 320, the pacing routines 324, the discomfort monitor 332, and the TENS routine 334) are described in greater detail below with reference to FIGS. 4-15. The treatment manager 314 and its constituent components may be implemented using hardware or a combination of hardware and software. For instance, in one example, the treatment manager 314 and its constituent components are implemented as software components that are stored within the data storage 304 and executed by the processor 318. In this example, the instructions included in the treatment manager 314 and its constituent components program the processor 318 to execute the processes described herein. In other examples, the treatment manager 314 and its constituent components may be application-specific integrated circuits (ASICs) that are coupled to the processor 318. Thus, examples of the treatment manager 314 and its constituent components are not limited to particular hardware or software implementations.

In some examples, the components disclosed herein, such as the treatment manager 314 and its constituent components, may read parameters that affect the functions performed by the components. These parameters may be physically stored in any form of suitable memory including volatile memory, such as RAM, or nonvolatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 308, that allow external entities to modify the parameters and thereby configure the behavior of the components.

The data storage 304 includes a computer readable and writeable nonvolatile data storage medium configured to store non-transitory instructions and data. In addition, the data storage 304 includes processor memory that stores data during operation of the processor 318. In some examples, the processor memory includes a relatively high performance, volatile, random access memory such as dynamic random access memory (DRAM), static memory (SRAM) or synchronous DRAM. However, the processor memory may include any device for storing data, such as a nonvolatile memory, with sufficient throughput and storage capacity to support the functions described herein. According to several examples, the processor 318 causes data to be read from the nonvolatile data storage medium into the processor memory prior to processing the data. In these examples, the processor 318 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system or data storage system.

The instructions stored on the data storage 304 may include executable programs or other code that can be executed by the processor 318. The instructions may be persistently stored as encoded signals, and the instructions may cause the processor 318 to perform the functions described herein. The data storage 304 also may include information that is recorded, on or in, the medium, and this information may be processed by the processor 318 during execution of instructions. The medium may, for example, be optical disk, magnetic disk or flash memory, among others, and may be permanently affixed to, or removable from, the medical device controller 300.

In some examples, the patient data 316 includes pacing parameter baselines associated with one or more patients, one or more pacing routines, or a combination of one or more patient parameter baselines and one or more pacing routines. The pacing parameter baselines may be stored as, for example, a series of tuples that include a parameter name that identifies a pacing parameter and a parameter value that specifies a baseline value of the identified pacing parameter to be used when a pacing routine is initiated for a patient. In some examples, each of the series of tuples may further include a patient name that identifies the patient and a pacing routine name that identifies a particular pacing routine to which the identified pacing parameter applies. The discomfort scale data 332 includes information representing one or more discomfort scales that may be used to quantify a level of discomfort being experienced by a patient. For example, the discomfort scale data 332 may include data representative of the Wong-Baker FACES® Pain Rating Scale.

As illustrated in FIG. 3, the treatment manager 314, the patient data 316, and the discomfort scale data 332 are separate components. However, in other examples, the treatment manager 314, the patient data 316, and the discomfort scale data 332 may be combined into a single component or re-organized so that a portion of the patient data 316 or the discomfort scale data 332 is included in the treatment manager 314. Such variations in these and the other components illustrated in FIG. 3 are intended to be within the scope of the examples disclosed herein.

The patient data 316 and the discomfort scale data 332 may be stored in any logical construction capable of storing information on a computer readable medium including, among other structures, flat files, indexed files, hierarchical databases, relational databases, or object oriented databases. These data structures may be specifically configured to conserve storage space or increase data exchange performance. In addition, various examples organize the patient data 316 and the discomfort scale data 332 into particularized and, in some cases, unique structures to perform the functions disclosed herein. In these examples, the data structures are sized and arranged to store values for particular types of data, such as integers, floating point numbers, character strings, arrays, linked lists, and the like.

As shown in FIG. 3, the medical device controller 300 includes several system interface components 302, 306, and 312. Each of these system interface components is configured to exchange, i.e. send or receive, data with one or more specialized devices that may be located within the housing of the medical device controller 300 or elsewhere. The components used by the interfaces 302, 306, and 312 may include hardware components, software components or a combination of both hardware and software components. Within each interface, these components physically and logically couple the medical device controller 300 to the specialized devices. This physical and logical coupling enables the medical device controller 300 to communicate with and, in some instances, power or control the operation of the specialized devices. These specialized devices may include physiological sensors, therapy delivery devices, and computer networking devices.

For instance, in some examples, the therapy delivery interface 302 includes waveform-shaping circuitry that receives pulse stream output and modifies signal characteristics of the pulse stream, e.g., pulse shape, polarity, and amplitude, to generate pacing pulses having configurable signal parameters. In these examples, the therapy delivery interface 302 delivers the pacing pulses to the therapy electrodes 330, which together externally deliver the pacing pulses to the patient for transcutaneous pacing of the patient's heart. Examples of the waveforms that may be delivered via the therapy delivery interface 302 are illustrated in FIGS. 10-15.

According to various examples, the hardware and software components of the interfaces 302, 306, and 312 implement a variety of coupling and communication techniques. In some examples, the interfaces 302, 306, and 312 use leads, cables or other wired connectors as conduits to exchange data between the medical device controller 300 and specialized devices. In other examples, the interfaces 302, 306, and 312 communicate with specialized devices using wireless technologies such as radio frequency or infrared technology. The software components included in the interfaces 302, 306, and 312 enable the processor 318 to communicate with specialized devices. These software components may include elements such as objects, executable code, and populated data structures. Together, these software components provide software interfaces through which the processor 318 can exchange information with specialized devices. Moreover, in at least some examples where one or more specialized devices communicate using analog signals, the interfaces 302, 306, and 312 further include components configured to convert analog information into digital information, and vice versa, to enable the processor 318 to communicate with specialized devices.

As discussed above, the system interface components 302, 306, and 312 shown in the example of FIG. 3 support different types of specialized devices. For instance, the components of the sensor interface 312 couple the processor 318 to one or more physiological sensors such as a body temperature sensors, respiration monitors, perspiration sensors, muscular contraction sensors, and electrocardiogram (ECG) sensing electrodes, one or more environmental sensors such as atmospheric thermometers, airflow sensors, video sensors, audio sensors, accelerometers, GPS locators, and hygrometers, or one or more motion detection sensors such as altimeters, accelerometers, and gyroscopes. In these examples, the sensors may include sensors with varying sampling rates, including wireless sensors. The sensor interface 312, as illustrated, is coupled to four ECG sensing electrodes that form a front-back (FB) electrode pair 326 and a side-side (SS) electrode pair 328. The sensor interface may include various circuitry to amplify the ECG signal detected by the electrodes, condition the received ECG signal, and/or digitize the ECG signals as described in U.S. Pat. No. 8,600,486, titled "METHOD OF DETECTING SIGNAL CLIPPING IN A WEARABLE AMBULATORY MEDICAL DEVICE" and issued on Dec. 3, 2013, which is hereby incorporated herein by reference in its entirety. It is appreciated that the particular number of ECG sensing electrodes coupled to the sensor interface 312 and/or the pairing of the ECG sensing electrodes may vary based on the specific implementation.

In some examples, the components of the therapy delivery interface 302 couple one or more therapy delivery devices, such as capacitors, defibrillator electrodes, pacing electrodes or mechanical chest compression devices, to the processor 318. It is appreciated that the functionality of the therapy delivery interface 302 may be incorporated into the sensor interface 312 to form a single interface coupled to the processor 318. Additional description regarding certain features, such as the waveform-shaping circuitry described above, that may be included in various examples is provided in U.S. Pat. No. 5,431,688, titled "METHOD AND APPARATUS FOR TRANSCUTANEOUS CARDIAC PACING" and issued on Jul. 11, 1995, which is hereby incorporated herein by reference in its entirety.

In some examples, the components of the network interface 306 couple the processor 318 to a computer network via a networking device, such as a bridge, router or hub. According to a variety of examples, the network interface 306 supports a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, UDP, DTN, HTTP, HTTPS, FTP, SNMP, CDMA, NMEA and GSM. It is appreciated that the network interface 306 of medical device controller 300 may enable communication between other medical device controllers within a certain range.

To ensure data transfer is secure, in some examples, the medical device controller 300 can transmit data via the network interface 306 using a variety of security measures including, for example, TLS, SSL or VPN. In other examples, the network interface 306 includes both a physical interface configured for wireless communication and a physical interface configured for wired communication. According to various examples, the network interface 306 enables communication between the medical device controller 300 and a variety of personal electronic devices including, for example, computer enabled glasses, wristwatches, earpieces, and phones.

In one example, the network interface 306 is also capable of transmitting and/or receiving information to assist in managing discomfort while treating a patient. This may be accomplished through one or more antennas integrated with or coupled to the network interface 306, and consequently coupled to the processor 318. For example, the one or more antennas may receive information representative of the pacing parameter baselines associated with the patient. The wireless signals received by the antennas may be analyzed by the processor 318 to generate pacing parameter baselines for the patient. The network interface 306 may also transmit signals descriptive of one or more generated pacing parameter baselines to an external system. For example, the medical device may transmit signals descriptive of the pacing parameter baselines associated with a patient to a computer system associated with a health care provider of the patient. The computer system associated with the health care provider may transmit signals descriptive of the pacing parameter baselines to one or more other medical devices employed to provide treatment to the patient.

Thus, the various system interfaces incorporated in the medical device controller 300 allow the device to interoperate with a wide variety of devices in various contexts. For instance, some examples of the medical device controller 300 are configured to perform a process of sending critical events and data to a centralized server via the network interface 306. An illustration of a process in accord with these examples is disclosed in U.S. Pat. No. 6,681,003, titled "DATA COLLECTION AND SYSTEM MANAGEMENT FOR PATIENT-WORN MEDICAL DEVICES," and issued on Jan. 20, 2004, which is hereby incorporated herein by reference in its entirety.

As illustrated in FIG. 3 by dashed lines, the sensor interface 312 is optional and may not be included in every example. For instance, a pacing device may employ the medical device controller 300 to deliver pacing pulses at a regular, set rhythm and receive data descriptive of the intensity of discomfort experienced by a patient via the user interface 308. Similarly, a pacing device may include the medical device controller 300 to provide alarm functionality but may not include a network interface 306 where, for example, the ambulatory defibrillator is designed to rely on the user interface 308 to announce alarms.

The user interface 308 shown in FIG. 3 includes a combination of hardware and software components that allow the medical device controller 300 to communicate with an external entity, such as a patient or other user. These components may be configured to receive information from actions such as physical movement, verbal intonation, or thought processes. In addition, the components of the user interface 308 can provide information to external entities. Examples of the components that may be employed within the user interface 308 include keyboards, strain gauges, pressure sensors, quartz and/or ceramic force sensors, piezoelectric transducers, rotating switches (spring loaded or otherwise), elastic deformable solids (e.g., a stress relief ball), mouse devices, buttons, microphones, electrodes, touch screens, printing devices, display screens, and speakers. In some examples, the electrodes include an illuminating element, such as an LED. In other examples, the printing devices include printers capable of rendering visual or tactile (Braille) output.

In some examples, the user interface 308 may be configured to provide information to external entities regarding a cardiac event experienced by the patient. For example, the user interface 308 may provide an alarm indicting that the patient has experienced an arrhythmia and is being paced. In these examples, the user interface may also receive input from the patient regarding any discomfort being experienced during pacing. For example, the user interface 308 may issue an alarm requesting the patient to interact with at least one element of the user interface 308 (e.g., push a button) to acknowledge the alarm and adjust parameters of the therapy (e.g., pacing pulses).

In some examples, functions of the treatment manager 314 may be divided between a baseline mode (e.g., a "learning mode"), where pacing parameter baselines are generated, and a management mode, where the pacing parameter baselines are used to administer treatment to the patient. As illustrated in FIG. 3, the treatment manager 314 is configured to execute various processes associated with the baseline mode and the management mode. The treatment manager 314 may receive requests to enter either the baseline mode or the management mode from another component (e.g., the user interface 308). In response to receiving a request to enter the baseline mode, the treatment manager 314 executes a baseline process, such as the baseline process 400 described below with reference to FIG. 4. In response to receiving a request to enter the management mode, the treatment manager 314 executes a management process, such as the management process 500 described below with reference to FIG. 5. It is appreciated that the particular architecture shown in FIG. 3 is for illustration only and other architectures and/or modes may be employed by the treatment manager 314.

Example Baseline Generation Process

In some examples, a treatment manager (e.g., the treatment manager 314 described above with reference to FIG. 3) is configured to generate baseline parameters associated with a patient, with a pacing routine, or a combination of both. The baseline parameters are indicative of a patient's tolerance for discomfort while being treated by execution of one or more pacing routines. The baseline process can yield information relating to a patient's discomfort threshold and further establish baseline values for the pacing parameters. In particular, the baseline process can yield a range of values for a discomfort parameter for the patient. As noted below, the baseline process can calculate a threshold value for the discomfort parameter from the range of values and use this threshold during active pacing management. In addition, the baseline process can determine baseline values for the pacing parameters to use as a starting point in the pacing management process.

Figure 4:
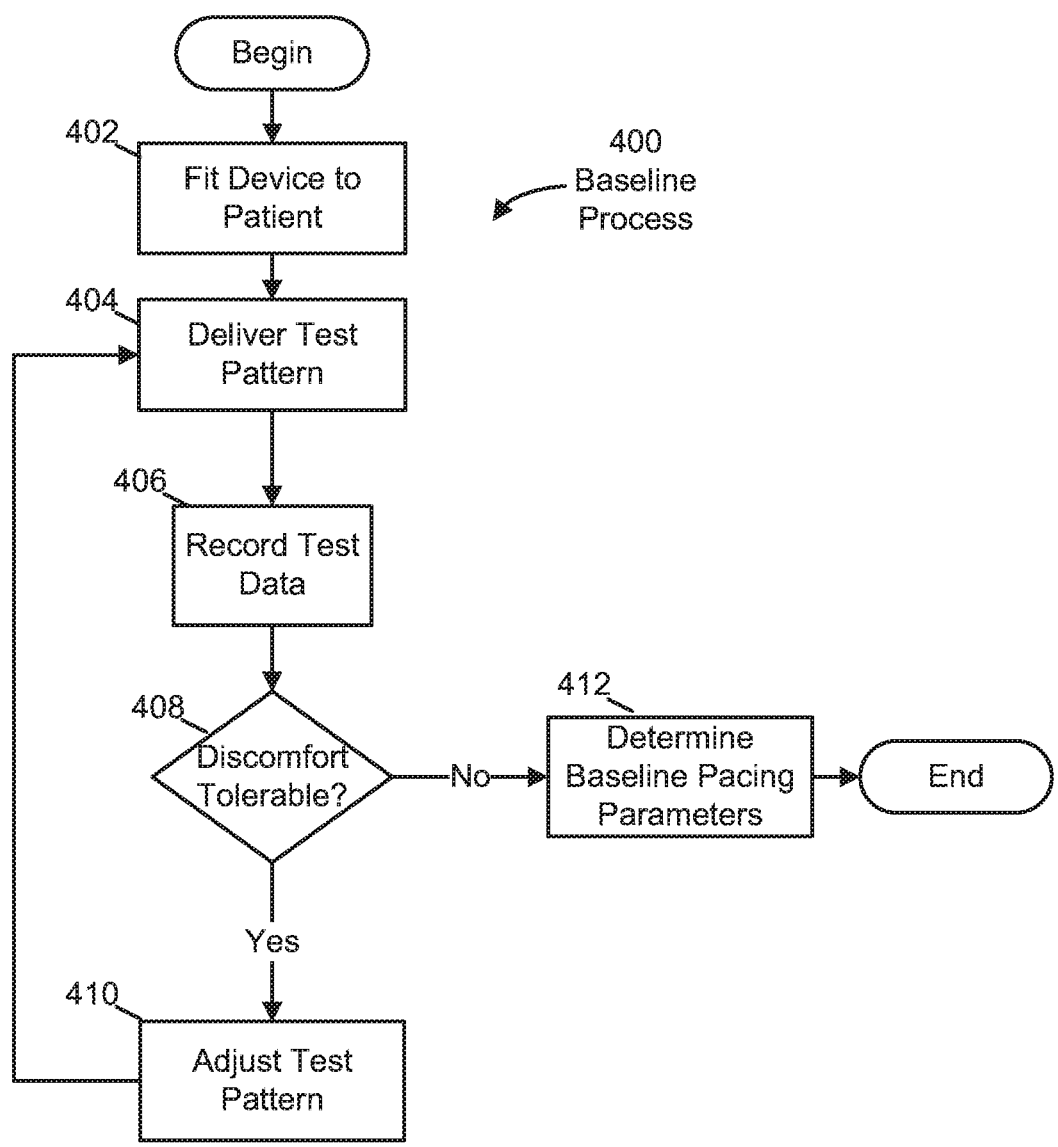
FIG. 4 is a flow diagram of one example baseline generation process.

FIG. 4 illustrates an example baseline process 400 performed by, for example, the treatment manager when the medical device is executing in baseline mode. In some examples, the baseline mode of the medical device is activated to initiate execution of the baseline process 400. The baseline process 400 may be performed before active patient monitoring begins via the management process 500 (described below with respect to FIG. 5). As discussed below, in some implementations, the baseline process 400 can be repeated periodically, e.g., once every two weeks, or when triggered by an external event (e.g., user-triggered event) or an internal event (e.g., automated detection of a triggering condition).

Example triggering conditions can include, without limitation, one or more of a change in patient profile information or data (e.g., through a manual or automated remote or local download process), device or user initiated periodic or aperiodic self-tests, mechanical impact detection (e.g., when the device is subject to forces beyond a predetermined threshold), tampering of the device, assembly and/or disassembly events involving the device, excess temperature and/or moisture events, battery change events, post-shock delivery (e.g., a period of time after a shock or pacing pulse has been delivered), an arrhythmia warning or alert event (e.g., when the patient is conscious and able to respond by pushing the response buttons), actuation of the response buttons (e.g., actuation of the buttons in a predetermined manner), changes in and/or tampering of the gel deployment mechanism, detected excessive cabling and/or device strains, error conditions thrown by software, and software updates.

During execution of the baseline process 400, the patient's tolerance for discomfort can be recorded and analyzed as described below. A user interface (e.g., the user interface 308 described above with reference to FIG. 3) can provide messages and interact with a user (either the patient or a caregiver) to allow the recording of the baseline pacing parameters. In some examples, the medical device notifies the user, via the user interface, upon completion of the baseline process 400. The patient (or caregiver) can abort the baseline process 400 at any time.

In one example, the baseline process 400 includes acts of fitting the medical device to a patient, delivering a pacing test pattern, calculating a level of discomfort experienced by the patient during delivery of the pacing test pattern, adjusting characteristics of the pacing test pattern, recording the test data, and optimizing pacing parameters. The baseline process 400 may also include transmitting the baseline parameters to an external system (e.g., a computer system of a health care provider associated with the patient) for storage, review, and analysis.

In act 402, the medical device is fitted to the patient. In some examples, the act 402 includes adjusting physical aspects of the medical device (e.g., a garment or belt) to fit snugly and securely to the patient's body. The act 402 may further include initiation of the baseline mode in the medical device via the user interface.

In act 404, the treatment manager initiates delivery of a test pattern to the patient that includes one or more pacing pulses delivered through one or more therapy electrodes (e.g., the therapy electrode pair 330 described above with reference to FIG. 3) and, optionally, one or more TENS pulses through one or more TENS electrodes (e.g., the TENS electrodes 336, the therapy electrode pair 330, and/or the pacing electrodes 338 described above with reference to FIG. 3). The pacing pulses and the TENS pulses included in the test pattern may have varied characteristics. These characteristics may be controlled by one or more pacing parameters (including TENS parameters) that are set by, for example, the treatment manager 314 discussed above with reference to FIG. 3. Example characteristics that may vary from pulse to pulse include pacing pulse amplitude, pacing pulse width, pacing pulse rate, pacing pulse waveform, pacing pulse period, pacing pulse duty cycle, pacing pulse ramp time constant, TENS pulse width, TENS pulse rate, TENS pulse amplitude, and TENS waveform. The pacing pulse amplitude may vary within a range of values between approximately 15 milliamps and 140 milliamps. The pacing pulse width may vary within a range of values between approximately 2 milliseconds and 40 milliseconds. The pacing pulse rate may vary within a range of values between approximately 20 pacing pulses per minute and 80 pacing pulses per minute. The pacing pulse period may vary within a range of values between approximately 20 microseconds and 500 microseconds. The pacing pulse duty cycle may vary within a range of values between approximately 10 percent and 100 percent. The pacing pulse ramp time constant may vary within a range of values between approximately 40 microseconds and 100 microseconds. The pacing pulse waveform may vary within a range of values including a rectilinear waveform, a pulse train waveform, a truncated exponential waveform, a variable waveform, and a biphasic waveform. The TENS pulse amplitude may vary within a range of values between approximately 0 milliamps and 200 milliamps. The TENS pulse width may vary within a range of values between approximately 0.001 milliseconds and 0.5 milliseconds. The TENS pulse rate may vary within a range of values between approximately 0.5 pulse per minute and 500 pulses per minute. The TENS pulse waveform may be selected to be any one of a rectilinear waveform, a pulse train waveform, and a biphasic waveform.

In various examples, different TENS stimulation modes may be used to ameliorate patient sensation and discomfort during cardiac pacing. For example, an optimal mode of TENS stimulation may be tested and adjusted during a baselining process of the medical device, e.g., a fitting period of a wearable defibrillator and/or pacing device. For example, one or more of the following TENS stimulation modes can be used in any of the examples described herein.

1. Constant or Continuous Mode.

In this example mode, a medical device administering TENS can constantly output a set pulse rate, pulse width and amplitude. The pulse rate can determine which theory of TENS should be administered (e.g., Gate or Endorphin theory). For example, the Gate theory of TENS implicates a high pulse rate (e.g., 80-150 Hz). Under the Gate theory, asymmetrical biphasic square wave pulses administered at high frequencies are understood to block a pain signal from an end of a nerve to the brain. For example, the Endorphin theory is implicated at lower pulse rates (e.g., 1-10 Hz). Under the Endorphin theory, a rubbing and/or pulsing sensation delivered through TENS can trigger a release of endorphins at the area when the TENS is applied.

In some implementations, the pulse width and amplitude can be set in accordance with the patient's comfort preferences (e.g., enough to feel the pulsing sensation, and just under the threshold of a muscle contraction). In an example, the TENS parameters can be set such that the patient is able to feel the stimulation while not finding it painful.

In some examples, the Constant Mode can be used to determine the baseline settings for the patient. Over time, the patient can acclimate to the perceived sensation of the output. In some implementations, in the Constant or Continuous Mode of operation, the patient may acclimate sooner because there is no modulation or change in the settings.

2. Pulse Rate Modulation Mode.

In this example mode based on varying a frequency of the pulses, the device can shift the frequency setting to, e.g., 50% of the set value over, e.g., 5 seconds. For example, if the pulse rate (in Hz) is set at 100 Hz, the device can be configured to shift the frequency downwards to about 50 Hz and, in some cases, upwards to about 150 Hz over a duration of, e.g., 5 seconds.

For example, if the pulse rate is set at 5 Hz, then the frequency can shift from about 3-8 Hz over, e.g., 5 seconds using the Endorphin theory. Accordingly, the patient may not acclimate to the sensation as quickly as in the Constant Mode.

3. Pulse Width Modulation Mode.

In this example mode, the sensations felt by the patient due to the TENS output of the device can be varied using shifts in pulse width. For example, the device can change the pulse width setting while holding the pulse rate (Hz) setting constant and determining what theory of TENS is to be used. The changing pulse width can keep the patient from acclimating to the TENS output over time. When the pulse width is increased (e.g., to about 50% over a 5 second cycle), the sensation typically feels stronger. As a result of this change, each individual pulse lasts longer. In an example, the pulse width setting can be set to be as high as possible without generating a visible muscle contraction or discomfort. Conversely, the pulse width setting can be decreased by up to, e.g., 50% of an initial setting over a 5 second cycle to ease the sensation felt by the patient.

4. Pulse Rate & Pulse Width Modulation Mode.

In this example mode, the device can be configured such that as the pulse rate (Hz) increases, the pulse width (uS) can be decreased and vice versa. The pulse rate (Hz) setting can determine whether the Gate or Endorphin Theory is to be applied. The pulse width can be used to determine how long each pulse is delivered, but both the pulse rate and pulse width can shift over time to prevent acclimation.

5. Cycled Burst Mode.

In this example mode, the pulse rate and pulse width settings can be configured to remain constant, but the amplitude can be dropped to be at or near zero for a first predetermined amount of time, e.g., 2.5 seconds. After this period elapses, the amplitude can be restored to the original amplitude setting for a second predetermined amount of time, e.g., another 2.5 seconds. This process can be repeated. In this manner, the device can create a "tapping" or "rubbing" sensation. For example, the pulse rate setting (Hz) can be in the 80-120 Hz range and be able to cause the release of endorphins.

6. Optimal Settings Mode.

Increase of set Pulse Width 40%, decrease of set Pulse Rate 45% and decrease of set Amplitude 10% over a 3 second period. Values return to original settings over the next 3 seconds.

In this example mode, the device can be configured to modulate some or all of the waveform settings as described herein to achieve maximum patient comfort. For example, when the pulse width shifts to higher settings (e.g., more aggressive sensation) the amplitude (or power level of the waveform) can be configured to drop, e.g., 10% of the original setting, to allow for an increase in the pulse width setting to ensure patient comfort. The pulse rate (e.g., characterized in Hz) can be used to determine whether the Gate or Endorphin theory of TENS is to be applied. In some examples, the frequency can be shifted e.g., up to 40%, to prevent patient acclimation.

In implementations, the device can be configured to intelligently shift all of the waveform settings to adjust in a predetermined pattern for maximizing patient comfort. For example, there can be a 90% shift in the pulse rate setting to allow for both the Gate and Endorphin Theories to be used within the same mode. For example, assuming that the initial pulse rate is set at 80 Hz, a 90% shift can allow for the pulse rate to swing from, e.g., 85 Hz (Gate Theory) to about, e.g., 10 Hz (Endorphin Theory). For example, one or more of the above modes (e.g., the Optimal Settings Mode) may be suited for patients with pain conditions relating to both parasympathetic and sympathetic nerve groups.

In some examples, the test pattern delivered by the initial execution of the act 404 includes one or more pacing pulses and one or more TENS pulses with mild characteristics that reside within the lower portions of each range of values described above. For instance, in at least one example, these one or more pacing pulses have characteristics set to the lower bound (minimum) within their respective ranges of values. In these examples, the TENS pulses are delivered within the interval between pacing pulses and provide background stimulation to the patient to distract the attention of the patient away from the discomfort caused by the pacing pulses.

In act 406, a discomfort monitor (e.g., the discomfort monitor 322) prompts for, receives, and records patient feedback regarding the test pattern through a user interface element as described herein. For example, the user feedback includes discomfort information acquired during execution of the test pattern for subsequent processing. In some examples, the discomfort information is recorded in data storage (e.g., the data storage 304 described above with reference to FIG. 3). This discomfort information may be received as voluntary or involuntary input from the user via the user interface or may be acquired from one or more other sensors coupled to a sensor interface (e.g., the sensor interface 312 described above with reference to FIG. 3). Examples of discomfort information received via the user interface include utterances (e.g., words, moans, groans, crying, or other expressions) and actuation of a discomfort measuring and/or indicating device (e.g., strain gauge, force sensor, push or squeeze button, rotary dial, elastic deformable solid). For example, the user can indicate a level of discomfort he or she feels by actuating any of one or more user interface elements as described herein. Examples of discomfort information received via other sensors (e.g., motion detection sensors, strain gauges in a garment) include movements (e.g., tensing of muscles, jerking, shuttering, flinching, changes in respiration) and lack of movement.

In some examples where the discomfort information is received as voluntary input, the discomfort monitor may prompt the user for the input by, for example, presenting a discomfort scale via the user interface. The discomfort scale may include numeric values and the user interface may request that the user rate the discomfort experienced on the numeric scale. The discomfort scale may also include graphical representations (e.g., faces) and the user interface may request that the user rate the discomfort experienced on the graphical scale. In some examples, the discomfort monitor infers the intensity of the discomfort based on the amount of pressure detected by the user interface or the period of time a user interface element remains actuated. For instance, in one example, the number of seconds that the user interface element remains actuated equates to a number of the Wong-Baker FACES® Pain Rating Scale.

In the act 408, the discomfort monitor determines whether the test pattern delivered in the previous iteration of the act 404 was tolerable to the patient. For example, the patient might indicate that the last administered test pattern is the maximum discomfort he or she is willing to tolerate by responding to a prompt presented by the user interface requesting this information. If the test pattern was tolerable, the treatment manager proceeds to the act 410. In some examples, if additional data is desired and the patient (or caregiver administering the baseline process 400) has not aborted the baseline process 400, a same or different (slightly higher or lower level) test pattern can be delivered to confirm the patient's tolerance level. If the test pattern was not tolerable, the treatment manager proceeds to the act 412. In some examples, the discomfort monitor determines whether the test pattern was tolerable at least in part by quantifying discomfort information. The discomfort information quantified by the discomfort monitor may have been acquired during execution of the test pattern in the act 404 or may have been received as voluntary input in response to one or more prompts provided to the user via the user interface within the act 406 (i.e., after execution of the test pattern in act 404 is complete). In some examples, the discomfort monitor assigns a value to the discomfort parameter based on the discomfort information. For instance, the discomfort monitor may store any of the following values as the value of the discomfort parameter: a value of a point on the discomfort scale selected via user input, a value calculated based on an amount of pressure exerted by the user on an element of the user interface (e.g., a quartz or ceramic force sensor, or a piezoelectric transducer), a value calculated based on a period of time a user interface element is actuated, or a value calculated based on motion of the patient or some other involuntary reaction to the test pattern exhibited by the patient. For example, in the case of a piezoelectric transducer, an active element (e.g., a polarized material such as quartz ($SiO_2$) or barium titanate ($BaTiO_3$)) can produce an electric field when the element changes dimensions as a result of an imposed mechanical force. For example, a force applied to a transducer or force sensor as described herein can be in a range between 0-25 lbs. (110 N). In some examples, when more force is applied, a resistance of the transducer can decrease. For example, in the case of a Flexiforce® pressure sensor from Tekscan®, a resistance range changes from substantially open circuit to about 50k ohms. When the force is applied, the resistance measured between leads of the transducer lowers until it reaches a maximum force value (e.g., 25 lbs). In an implementation, the force applied may be in the form of a user squeezing two opposing surfaces of a sensor. The examples described herein are not limiting and other kinds of force sensors can be used.

For example, in the case of a ceramic or quartz force sensor, a piezoelectric transduction mechanism can be coupled to a integrated circuit, e.g., a voltage or charge amplifier. The applied force can produce a quantity of charge, e.g., $\Delta q$. The charge accumulates in the crystal capacitance and forms a voltage according to the law: $\Delta V = \Delta q / C$. For example, a low capacitance quartz sensing element can produce a high voltage output. In such applications, a MOSFET voltage amplifier can be used to control the output voltage. Ceramic sensing elements can exhibit a high charge output, and so can be coupled to a charge amplifier.

In the manner described above, a discomfort parameter can be calculated to correspond to a force sensed by a force sensor. For instance, the discomfort parameter based on the force sensor can be scaled to be within a range of 1-10 units (e.g., the parameter can be configured in accordance to a predefined numerical relationship to an output voltage level of the force sensor).

In some examples, the discomfort monitor determines whether the test pattern was tolerable by comparing the value of the discomfort parameter to a discomfort threshold value. This discomfort threshold value may be a configurable parameter of the medical device that may be adjusted to each particular patient. For instance, in one example, the discomfort threshold is set to a value of 4 in the Wong-Baker FACES® Pain Rating Scale. Similarly, on the force sensor scale described above, the discomfort threshold may be set to a value of 5. It is appreciated that the patient discomfort scale and threshold as described above can vary depending on the patient's personal preferences and/or the caregiver's recommendations. For example, the scale employed may be a percentage scale (e.g., 1-100) and a threshold can be set to be 40 percent of full range. In some examples, color coded zones may be used to indicate the discomfort scale, e.g., a red zone corresponding to maximum intensity, a yellow zone corresponding to minimal discomfort, and a green zone corresponding to discomfort in the middle of the range.

In some examples, the discomfort monitor determines that the test pattern was tolerable where the value of the discomfort parameter maintains a predefined relationship with a discomfort threshold value (e.g., where the value of the discomfort parameter does not transgress the discomfort threshold value). In these examples, the discomfort monitor determines that the test pattern was not tolerable where the value of the discomfort parameter does not maintain a predefined relationship with the discomfort threshold value (e.g. where the value of the discomfort parameter is equal to or transgresses the discomfort threshold value). It is appreciated that, depending on the specific calculations used, a discomfort threshold value may be transgressed by a value that is greater than or less than the discomfort threshold value.

In act 410, the discomfort monitor adjusts the test pattern. In some examples, the discomfort monitor adjusts the test pattern by varying characteristics of pulses included in the test pattern. In these examples, each characteristic of each pulse may be varied within its respective range as described above with reference to the act 404. In general, the discomfort monitor adjusts one or more characteristics upward within their respective ranges to increase the efficacy of each pulse. For instance, in at least one example, the discomfort monitor adjusts each characteristic upward by a step value specified by a configurable parameter of the medical device. One effect of this approach is to shorten the overall execution time of the baseline process 400. Another effect of this approach is to collect fewer test data points for subsequent analysis. In another example, the discomfort monitor adjusts only one characteristic upward by the step value. One effect of this approach is to more precisely measure the effect that each characteristic has on the patient. Another effect of this approach is to collect more test data points for subsequent analysis. In another example, the discomfort monitor adjusts some characteristics upward by the step value and adjusts others downward by a step value to establish discomfort parameter samples for a broad mix of characteristics. It is appreciated that the step values by which each characteristic is adjusted may reside on continuums having different scales. Examples of these scales include linear scales, log scales, and exponential scales.

Pacing discomfort may stem from at least two sources: 1) electrical stimulation of the cutaneous nerves; and 2) skeletal muscle contraction, particularly the intercostal muscles. Electrical stimulation can feel to a patient like pin-pricks on the skin, while skeletal muscle contraction can feel like getting hit in the chest with a hammer or a fist. In examples, a degree of cutaneous nerve stimulation can be difficult to measure non-invasively but may be easier to ameliorate than the skeletal muscle contraction. The cutaneous nerve stimulation may be reduced by, for instance, increasing the resistivity of the electrically conductive gel that is against the skin. Thus, some examples as described herein can include and deploy electrically conductive gel for pacing, such that a resistivity of the gel against the skin can be varied in accordance with patient discomfort For example, in some implementations, the impedance as seen by the pacing electrodes can be varied as one of the pacing routine parameters in response to the patient's discomfort management as described herein.

In some example implementations, the device can measure a degree of skeletal muscle stimulation and use the measurement to determine the discomfort parameter. For instance, in some examples, the discomfort monitor uses the value of the measurement as the value of the discomfort parameter. In some examples, the discomfort monitor calculates the discomfort parameter using the value of the measurement and other factors, such as voluntary input as described in detail herein.

In some examples, the discomfort monitor measures the degree of skeletal muscle contraction using a flexible strain gauge adhered to the patient's skin. The strain gauge may be composed of, for instance, a bi-layer, laminate construction of polyvinylidene fluoride (PVDF), also sometimes called Kynar. The bi-layer construction generates a voltage inversely proportional to the radius of curvature of the strain gauge laminate sheet. Thus the electrical voltage generated by the strain gauge deformation will be proportional to the degree of intercostal muscle contractions. Alternatively, the measure of the degree of intercostal muscle contraction may be accomplished by having at least two motion sensors such as micro-electro-mechanical systems (MEMS) accelerometers affixed to adjacent ribs and the relative motion measured in, e.g., the 0-500 millisecond, time period subsequent to the electrical pulse.

The patient may also enter a perceived discomfort via the user interface, which is configured to receive this input. In these examples, the discomfort monitor can be configured to store the two values: e.g., the patient-perceived discomfort on the discomfort scale and the measured skeletal muscle contraction. This sampling can be repeated for two or more pacing parameters to create a series of two or more vectors composed of at least a perceived discomfort score (PDS) and a measure of skeletal muscle contraction (SMC). In these examples, the discomfort monitor generates a lookup table from the multiple values of PDS/SMC vectors that were generated using the multiple instances of pacing parameters. The pacing parameter may be pacing current, with the PDS/SMC vector pairs generated, for instance, at 10-100 mA in 10 mA increments. An example of such a lookup table is shown below:

| | Current | | | | | | | | | |
|---|---|---|---|---|---|---|---|---|---|---|
| | 10 | 20 | 30 | 40 | 50 | 60 | 70 | 80 | 90 | 100 |
| PDS | 0 | 2 | 5 | 6 | 8 | 9 | 10 | 10 | 10 | 10 |
| SMC | 0.35 | 1.2 | 1.7 | 2.3 | 2.7 | 3.2 | 5.6 | 7.7 | 9.2 | 11.3 |

Thus, where the wearable medical device determines that the patient is in need of pacing, the wearable medical device initiates pacing with the pacing current amplitude that corresponds to a low level of perceived discomfort of that particular patient. The correspondence of PDS and SMC levels with changes in pacing amplitude or other parameters can vary from patient to patient. As such, an initial baselining process can be used to calibrate the pacing parameter values with a particular patient's perception of discomfort.

Next, the wearable medical device checks a patient physiological parameter, such as the ECG or pulse oximetry. In some examples, the wearable medical device checks the physiological parameter by analyzing information transmitted by another wearable device, such as an iWatch (from Apple, Inc., of Cupertino Calif.), that is in wireless communication with the wearable medical device via the sensor interface. Through this analysis, the wearable medical device determines whether pacing has been effective and is, therefore, generating blood flow. If the pacing is effective, then the wearable medical device identifies the current pacing parameter values as being an effective level for pacing that is still comfortable for the patient.

If, however, a pulse or other measure of pacing effectiveness is not detected in one or more of the physiological parameter measurements, then the wearable medical device increases the amplitude of a pacing parameter, for example, pacing current, to the next setting. This will likely result in a higher level of discomfort but also a higher chance of being effective. The wearable medical device may repeat this process until pacing effectiveness has been achieved. More elaborate search methods may be employed, such as a binary search, to minimize the amount of time required to achieve effective pacing.

Alternatively, instead of a lookup table, the wearable medical device may generate a mathematical relationship—the "discomfort estimation function" (DEF) —between the pacing parameters, SMC, and an estimate of discomfort. The mathematical relationship may be interpolation of the data points in the lookup table. The interpolation may be linear or nonlinear as well as employ splines. The wearable medical device may generate the mathematical relationship using one or more techniques such as logistic regression, neural networks, or fuzzy logic.

It has been found that patient's perceptions of discomfort shift with varying external circumstances as well as internal mental and emotional status. In another embodiment, the wearable medical device estimates the patient's actual discomfort level by analyzing the SMC measurements in real time (or near real time) while pacing is occurring.

In some examples, the user interface includes one or more elements that receive input indicating the discomfort level being experienced by the patient during actual pacing process execution, rather than as a result of operating in a baseline or test mode. In these examples, the discomfort monitor stores these discomfort levels for a particular set of pacing parameters during actual pacing as a secondary, calibrating set that modifies the original discomfort levels acquired during the baseline process 400. The wearable medical device can use these additional data points to provide a more accurate DEF estimate. For instance, the wearable medical device may store the data points and calculate a new DEF in real time (or near real time). In some examples, the wearable medical device may transmit the actual pacing discomfort levels to a server and database that stores the results for that patient as well as many other patients. In these examples, the server may execute the optimization and download new pacing parameter values to the wearable medical device at some point after the clinical event.

In act 412, the discomfort monitor uses the test data to determine baseline values for the pacing parameters. In an example, the discomfort monitor can select the baseline pacing parameter values for the patient based on a predetermined relationship (e.g., a formula) between the patient's range of discomfort parameters, the threshold discomfort, and underlying pacing parameters. For example, the baseline pacing parameter values can be the pacing parameter values corresponding to a discomfort parameter value that is a fraction of the patient's discomfort threshold value, e.g., 25-75% of the patient discomfort threshold.

In some implementations, the baseline pacing parameter values can be selected without reference to the patient's discomfort threshold. For example, the baseline pacing parameter values can be a set of values selected at a lower (minimum) bound of the ranges of values for the pacing parameters. For example, the baseline pacing parameter values can be a set of values selected at a lower (minimum) bound of the ranges of values for a first set of pacing parameters (e.g., pulse amplitude and pulse width), and a values selected around a middle of the range of values for a second set of pacing parameters (e.g., pulse rate and/or pulse duty cycle). It is appreciated that the baseline pacing parameter values can be selected by any process reflecting the patient's tolerance and are not limited to the examples described above. In some cases, where a baseline process 400 is not available, a set of values can be selected as default values in accordance with the principles described herein.

In some implementations, the baseline process 400 may set values for only a subset of the parameters. For example, the baseline process 400 may set values for only an amplitude and a pulse width. The remaining parameters may either be assigned default values in accordance with the principles described herein, or the manually provided by the patient and/or caregiver, e.g., via a user interface.

In one example, the discomfort monitor determines the baseline values of the pacing parameters by solving an optimization problem. In this example, the discomfort monitor maximizes the efficacy of each pacing routine executable by the treatment manager subject to the range constraints described with reference to the act 404 above and subject to the value of the discomfort parameter maintaining a predefined relationship with to the discomfort threshold value.

For instance, according to one example, for all pacing pulses 1 to n in a pacing routine p, let the following variables represent the following characteristics of pacing pulses and TENS pulses, where $1 \leq i \leq n$. It is appreciated that each of the pacing and TENS pulse characteristics in Table 1 and Table 2 below may be controlled by a pacing parameter set by the medical device controller (e.g., controlled by treatment manager 314 of medical device controller 300).

TABLE 1

| Variable | Pacing Pulse Characteristic |
| --- | --- |
| $a_i$ | amplitude of pulse i |
| $w_i$ | width of pulse i |
| $r_i$ | rate of pulse i |
| $v_i$ | waveform of pulse i |
| $p_i$ | period of pulse i |
| $d_i$ | duty cycle of pulse i |
| $c_i$ | ramp time constant of pulse i |

TABLE 2

| Variable | TENS Pulse Characteristic |
| --- | --- |
| $x_i$ | amplitude of pulse i |
| $y_i$ | width of pulse i |
| $z_i$ | rate of pulse i |
| $q_i$ | waveform of pulse i |

Given these variables, the optimization problem to maximize the efficacy of the baseline parameters may be formulated as follows:

max $\Sigma_{i=1}^{n}$ f(i), where f(i) is the efficacy of a pacing pulse resulting from the combination of pacing pulse characteristics $(a_i, w_i, r_i, v_i, p_i, d_i, c_i)$;

subject to:

$d(i) \leq t$ for all i, where d(i) is the discomfort parameter resulting from the pacing pulse characteristics $(a_i, w_i, r_i, v_i, p_i, d_i, c_i)$ in combination with the TENS pulse characteristics $(x_i, y_i, z_i, q_i)$ and t is the value of the discomfort threshold;

15 milliamps $\leq a_i \leq$ 200 milliamps;

0.5 milliseconds $\leq w_i \leq$ 40 milliseconds;

20 pacing pulses per minute $\leq r_i \leq$ 200 pacing pulses per minute;

20 microseconds $\leq p_i \leq$ 500 microseconds;

10 percent $\leq d_i \leq$ 100 percent;

40 microseconds $\leq c_i \leq$ 100 microseconds;

$v_i \in$ {rectilinear, pulse train, truncated exponential, variable, biphasic};

0 milliamps $\leq x_i \leq$ 200 milliamps;

0.001 milliseconds $\leq y_i \leq$ 0.5 milliseconds;

0.5 pulses per minute $\leq z_i \leq$ 500 pulses per minute; and $v_i \in$ {rectilinear, pulse train, biphasic};

In some examples, the discomfort monitor approximates d(i) by fitting a mathematical function to the test data recorded during the act 406 (by, for example, logistic regression analysis). In these examples, the discomfort monitor uses the fitted expression as a constraint in the optimization problem as described above and solves the optimization problem to generate a set of baseline parameter values $(a_b, w_b, r_b, v_b, p_b, d_b, c_b, x_b, y_b, z_b)$ for each pacing routine p executable by the treatment manager. The baseline process 400 ends after execution of the act 412.

Processes in accord with the baseline process 400 enable patients to establish an individualized set of baseline values for the pacing parameters. The processes enable execution of tolerable external pacing routines, thereby providing patients with a measure of control not afforded by conventional external pacing processes. Accordingly, the patient may initially be administered a pacing routine in accordance with the established baseline values (e.g., as a set of default values for the pacing parameters). The patient may then control the pacing parameters through one or more user interface elements as described herein. In the event the patient is unable to provide voluntary feedback, the medical device can use other sensor information to determine and evaluate the efficacy of the pacing routine as described herein.

In some examples, the optimization problem described above may be applied to test data that represents a population of patients to determine baseline values for the "average" patient. These "average" baseline values may be stored as default values to be used where the baseline process 400 has not been executed or where the baseline process 400 is not available to be performed for a patient prior to commencement of patient monitoring.

In one example, the following baselining procedure may be employed.

First, set pace pulse width to 75 ms, no TENS, pace pulse ramp to minimum (e.g. 0.01 milliseconds). These settings provide for maximum effectiveness of pace pulse.

Second, for pace pulse amplitudes from 10 mA to 150 mA in increments of 10 mA, check to see if there is pace pulse capture and obtain the discomfort measure from the patient for each mA setting.

Third, for the pace current setting that is at least 20 mA higher than the first setting at which pacing capture was detected ("test pace current setting"), adjust the pace ramp from the minimum ramp to a ramp of 75 ms in steps of 15 ms. Assess for pace capture at each setting and the user's assessment of the discomfort measure. Ramp time for step 4 ("test ramp time") below is the ramp time value for which there has been no loss of pace capture and results in the least amount of patient discomfort.

Fourth, setting the device to the test pace current setting and the test ramp time, decrease the pace pulse width from 75 ms down to 5 ms in increments of 10 ms. The "test pace pulse width" is the pace pulse width that is 20 ms larger than the minimum pulse width where capture was still achieved.

Using the test pace current setting, test ramp time, and test pace pulse width, determine the response of the discomfort measure to variation in the TENS parameters.

Figure 17:
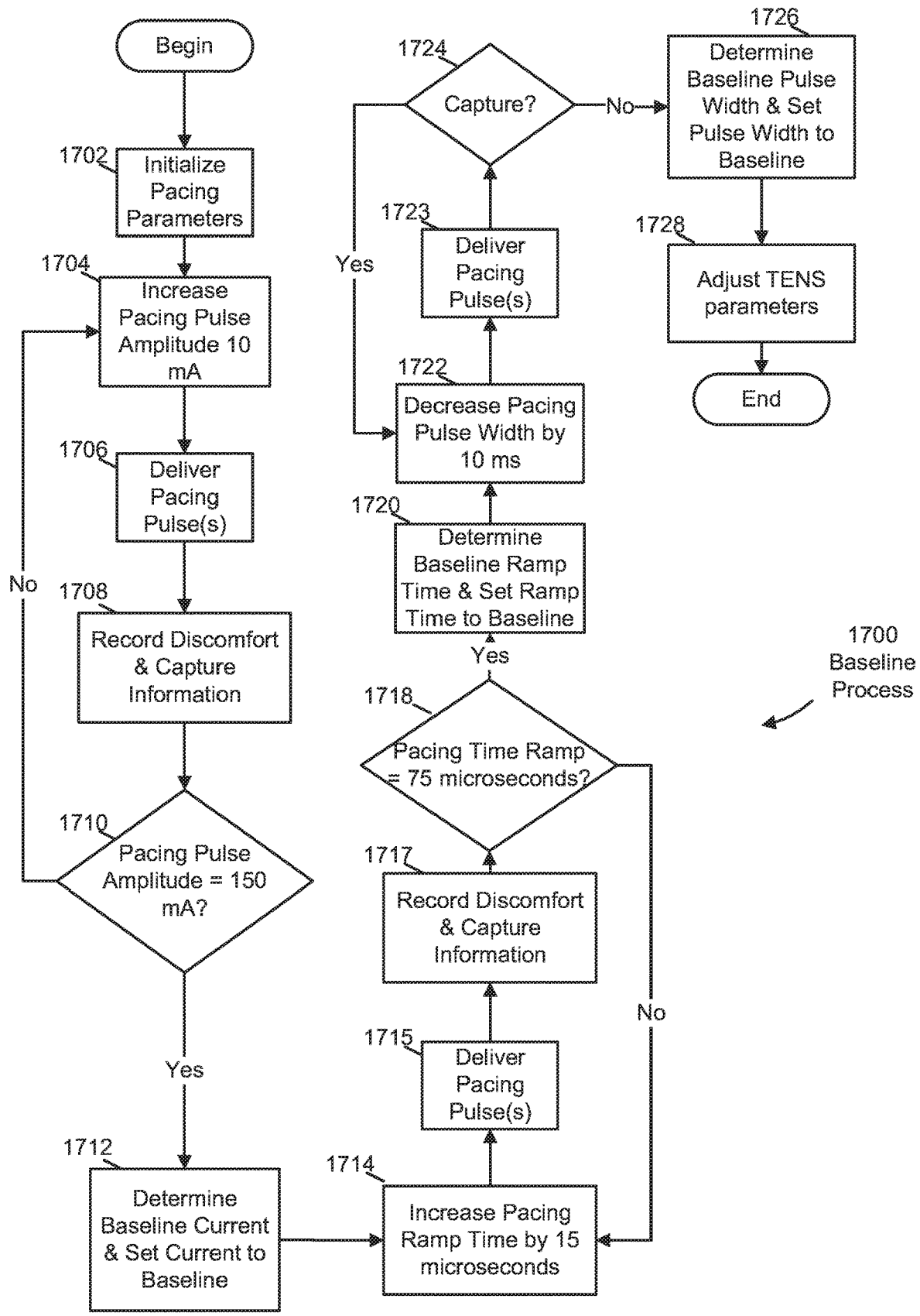
FIG. 17 is a flow diagram of one example baseline generation process.

FIG. 17 illustrates an example baseline process 1700 in accordance with an implementation based on the above process. For example, the baseline process 1700 begins at 1702 where the discomfort monitor (e.g., discomfort monitor 322 of treatment manager 314 of FIG. 3) sets the pacing pulse width to 75 milliseconds, sets the pacing pulse ramp to minimum (e.g. 0.01 milliseconds), and sets the active TENS routine to none (e.g., no TENS pulses). In implementations, such settings can provide for maximum effectiveness of the pacing routine.

In act 1704, the discomfort monitor increases the pacing pulse amplitude by a predetermined amount, e.g., in increments of 10 mA. In some implementations, both or either of the initial pacing pulse amplitude and the predetermined increment in the pacing pulse amplitude can be governed by user-configurable parameters. For example, a default value for the initial pacing pulse amplitude of 10 mA can be programmed into the device (either during the initial device configuration or prior to shipping the device to the caregiver). Similarly, a default value for the increment in pacing pulse amplitude of 10 mA can be programmed into the device. In implementations, the caregiver may be able to modify these values for his or her patient. Once the initial pacing pulse amplitude value is set, the discomfort monitor can gradually increase the amplitude according to the predetermined increment values. For example, the discomfort monitor can increase the pacing pulse amplitude by 10 mA in each iteration. In some examples, the discomfort monitor can be configured to change the increment value for one or more iteration. For instance, after about 10-12 iterations, the discomfort monitor may increase the amplitude by only 5 mA for each successive iteration.

In act 1706, the wearable medical device delivers one or more pacing pulses in accordance to the pacing routine parameters set in acts 1702-04. For example, the device may be configured to deliver a preconfigured number of pulses (e.g., 1-3 or more pulses).

In act 1708, the discomfort monitor records discomfort information in accordance with the principles described herein. Further, the cardiac monitor records capture information, e.g., checks to see if there is pacing pulse capture using one or more techniques described herein. The recorded information is associated with the pulse amplitude and either stored locally (e.g., on a memory disposed within the device, such as, data storage 304 of FIG. 3) or transmitted to a remote processing site.

In act 1710, the discomfort monitor determines whether the pacing pulse amplitude is equal to a predetermined maximum amplitude value, e.g., 150 milliamps. If the pacing pulse amplitude is not equal to the predetermined maximum amplitude value of 150 milliamps, the discomfort monitor returns to the act 1704. If the pacing pulse amplitude is equal to the predetermined maximum amplitude value of 150 milliamps, the discomfort monitor proceeds to act 1712.

In act 1712, the discomfort monitor determines the baseline pacing pulse amplitude by identifying the first pacing pulse amplitude that resulted in capture and adding a certain current value, e.g., at least 20 milliamps, to the identified pacing pulse amplitude. Also in act 1712, the discomfort monitor sets the pacing pulse amplitude to the determined baseline pacing pulse amplitude, e.g., the test pace current setting referenced above.

In act 1714, the discomfort monitor increases the pacing ramp time by a predetermined amount, e.g., 15 microseconds.

In act 1715, the wearable medical device delivers one or more pacing pulses and in act 1717, the discomfort monitor records discomfort information and the cardiac monitor records capture information.

In act 1718, the discomfort monitor determines whether the pacing ramp time is equal to a predetermined maximum ramp time value of, e.g., 75 microseconds. If the pacing ramp time is not equal to the predetermined maximum ramp time value of 75 microseconds, the discomfort monitor returns to the act 1714. If the pacing ramp time is equal to predetermined maximum ramp time value of 75 microseconds, then the discomfort monitor proceeds to act 1720.

In the act 1720, the discomfort monitor determines the baseline ramp time by identifying the ramp time value for which there was no loss of pacing capture and for which the patient experiences the least amount of discomfort. Also in the act 1720, the discomfort manager sets ramp time to the determined baseline ramp time value, e.g., the test ramp time referenced above.

In act 1722, with the device set to the test pace current setting and the test ramp time in accordance with the acts described above, the discomfort manager decreases the pacing pulse width by a predetermined amount, e.g., 10 microseconds. For example, the initial pacing pulse width is set to be 75 ms, and is decreased in the aforementioned steps of 10 ms to a minimum pacing pulse width value of 5 ms. In act 1723, the wearable medical device delivers one or more pacing pulses. In act 1724, the cardiac monitor determines whether the pacing pulses resulted in capture. If the pacing pulses resulted in capture, the discomfort monitor returns to the act 1722. If the pacing pulses did not result in capture, the discomfort monitor determines the baseline pulse width value, e.g., the test pace pulse width, by identifying a smallest pacing pulse width that resulted in capture and adding a predetermined value, e.g., 20 milliseconds, to the identified pacing pulse width.

In act 1728, with the device set to the above test pace current setting, test ramp time, and test pace pulse width in accordance with the acts described above, the discomfort manager applies TENS routines with various parameters as described above, acquires and records discomfort information for each, and identifies the TENS routine parameters that are associated with the least patient discomfort.

From the set of data generated from the baseline process 1700 above, a mathematical function can be derived that describes the relationship between the pacing parameters (including, in some implementations, the TENS parameters) and both discomfort and pacing effectiveness, and known statistical methods such as response surface methodology and logistic regression can be used to find the optimal trade-off between minimizing discomfort and maximizing pacing effectiveness. In one example, a process such as response surface methodology (RSM) can be used to explore the relationships between several explanatory variables and one or more response variables in implementing a pacing effectiveness/patient discomfort program. For example, a sequence of designed experiments can be used to obtain an optimal response using at least a second-degree polynomial model. For example, a first-degree polynomial model can be used to determine which explanatory variables may have an impact on the response variables of interest. A more complicated design, such as a central composite design, can be implemented to estimate a second-degree polynomial model for use in the optimization of the parameters as described herein (e.g. to maximize, minimize, or attain a specific target for the parameters).

Example Pacing Management Process

Figure 5:
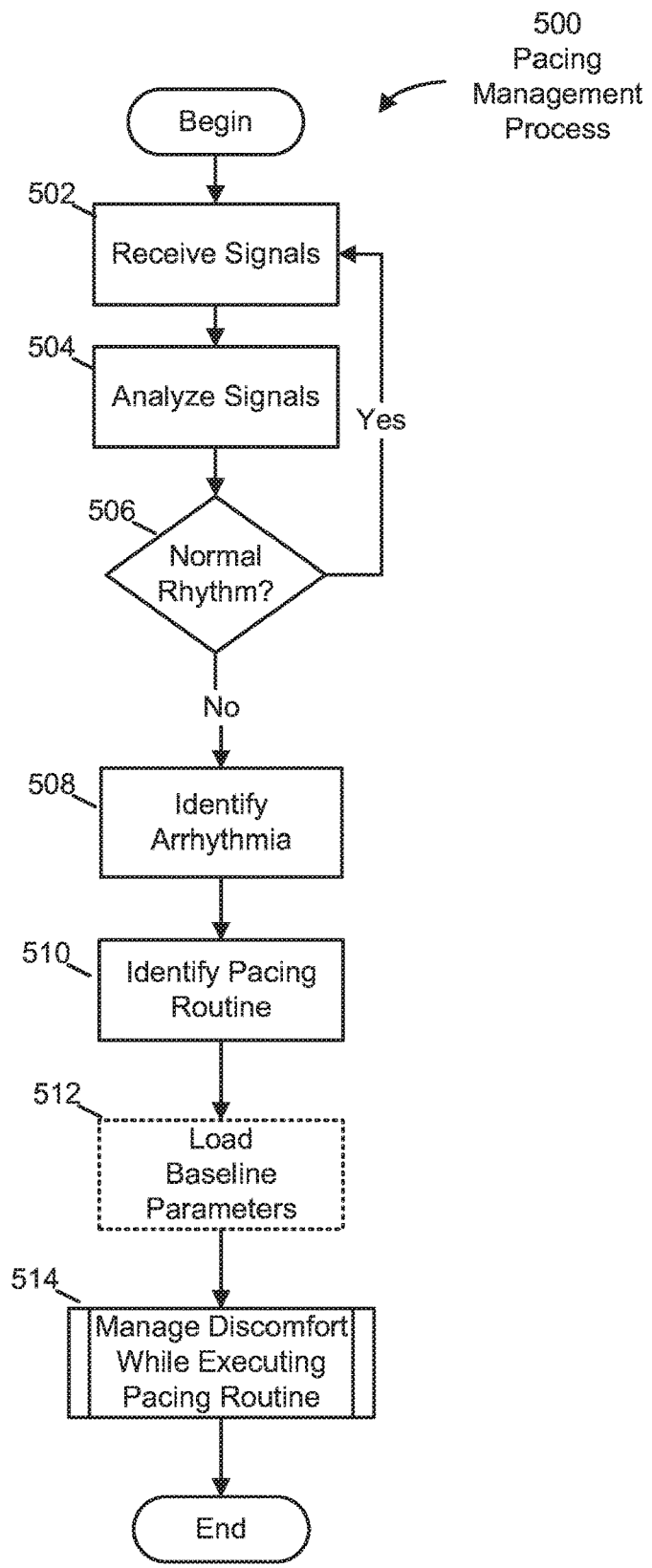
FIG. 5 is a flow diagram of one example pacing management process.

As described above, various examples implement processes through which a medical device manages discomfort experienced by a patient during execution of a pacing routine. FIG. 5 illustrates one such pacing management process 500. As shown, the pacing management process 500 includes acts of receiving signals, analyzing the received signals, determining whether the analyzed signals represent a normal cardiac rhythm, identifying a pacing routine to treat an arrhythmia, loading baseline pacing parameters associated with the patient and the identified pacing routine, and managing execution of the identified pacing routine.

In act 502, the treatment manager receives electrode signals generated from detectable characteristics of the patient's cardiac function via one or more electrodes (e.g., the electrode pairs 326 and 328 described above with reference to FIG. 3). In act 504, the treatment manager analyzes the received signals using a cardiac monitor (e.g., the cardiac monitor 320 described above with reference to FIG. 3).

In act 506, the cardiac monitor determines whether the patient's cardiac rhythm is normal. If so, the pacing management process 500 returns to the act 502. Otherwise, the cardiac monitor identifies an arrhythmia in act 508. In act 510, the treatment manager determines whether the identified arrhythmia is treatable by either a defibrillating shock or a pacing routine. Where the treatment manager detects an arrhythmia that requires defibrillation, the treatment manager may begin a defibrillation treatment protocol potentially culminating in a defibrillating shock. Where the treatment manager determines that the identified arrhythmia is treatable by an identified pacing routine (e.g., from the pacing routines 324 described above with reference to FIG. 3), the treatment manager proceeds to act 512. The treatment manager may determine that the identified arrhythmia is treatable by the identified pacing routine by, for example, referring to one or more configurable parameters stored in a data storage (e.g., the data storage 304 described above with reference to FIG. 3) that associates arrhythmias to pacing routines.

In the act 512, the treatment manager loads baseline pacing parameters associated with the patient and identified pacing routine. These baseline pacing parameters may identify a TENS routine (e.g., from the TENS routines 334 described above with reference to FIG. 3) to be executed in conjunction with the identified pacing routine. As illustrated in FIG. 5 by dashed lines, the act 512 is optional and may not be executed in some examples where the baseline process 400 has been omitted. For example, as indicated below, if a baseline process was not completed, then default values can be used for the parameters of the pacing routine.

In the act 514, the treatment manager executes the identified pacing routine and any associated TENS routines as described below with reference to FIGS. 6-8 and 16 and the pacing management process 500 ends. The pacing management process 500 may execute repeatedly during operation of the medical device to monitor and treat the patient as needed. The following sections describe processes that may be executed within the act 514.

Example Direct Control Pacing Process

Figure 16:
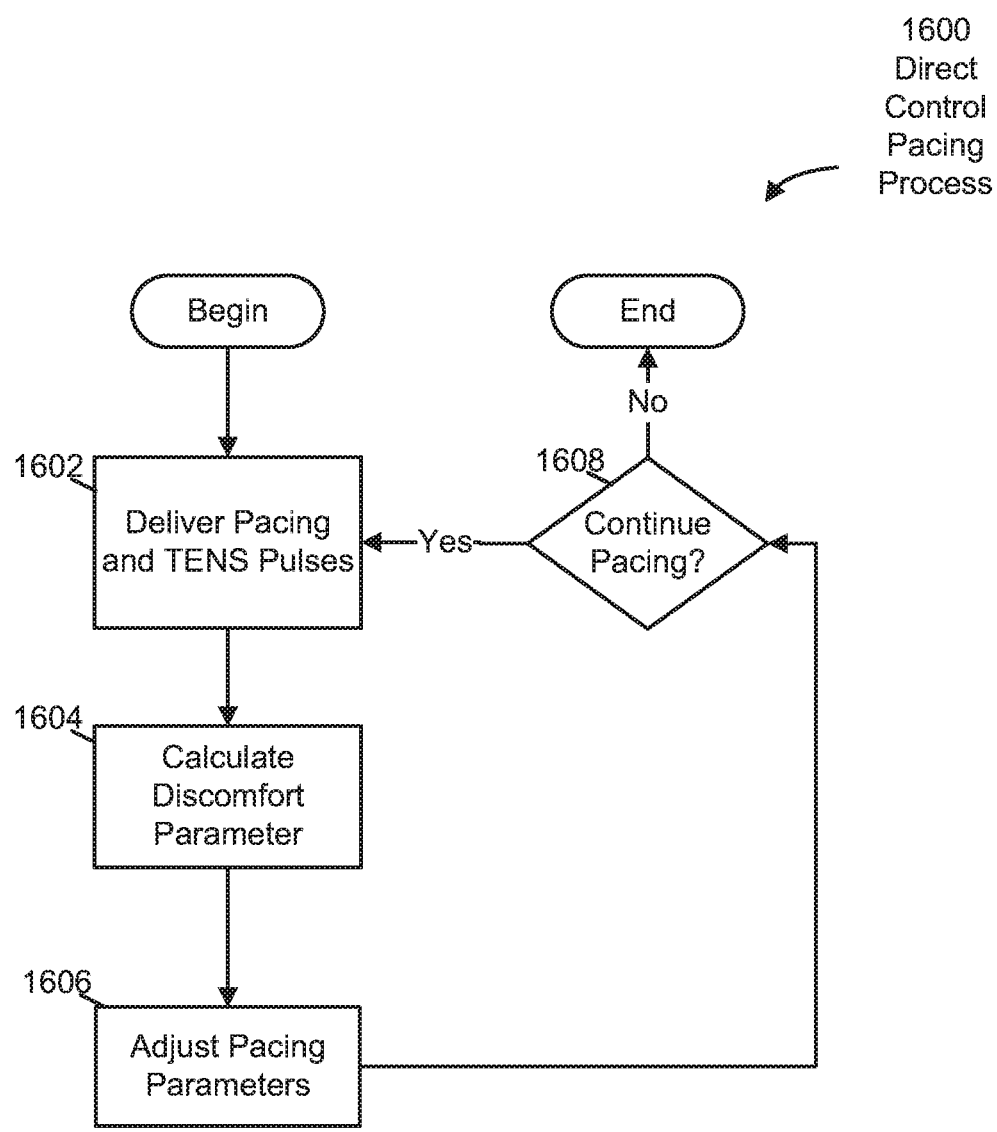
FIG. 16 is a flow diagram of one example managed pacing routine.

In one example of the act 514, the treatment manager is configured to provide the patient with direct control of a pacing routine. FIG. 16 illustrates one example of a managed pacing routine 1600 that is executed within the act 514. The managed pacing routine 1600 executes a direct control pacing process that is managed to decrease discomfort relative to conventional pacing processes. As shown in FIG. 16, the managed pacing routine 1600 includes acts of delivering pacing pulses, calculating a discomfort parameter, adjusting pacing parameters, and determining whether pacing should continue.

In act 1602, the treatment manager delivers one or more pacing pulses and monitors patient discomfort. In some examples, the treatment manager delivers the one or more pacing pulses to the patient according to the baseline parameters loaded in the act 512 described above with reference to FIG. 5. In examples where the act 512 has been omitted, the treatment manager delivers one or more pacing pulses to the patient in accord with default pacing parameters stored in the data storage. In at least one example, the default pacing parameter values are each set at the upper bound (maximum) of each range of values. In some examples, the default pacing parameter values may be a set of values selected at a lower (minimum) bound of the ranges of values. In some examples, the default pacing parameter values may be a set of values selected at a lower (minimum) bound of the ranges of values for a first set of pacing parameters (e.g., pulse amplitude and pulse width), and a values selected around a middle of the range of values for a second set of pacing parameters (e.g., pulse rate and/or pulse duty cycle). It is appreciated that one or more combinations of default pacing parameter values for each pacing parameter can be selected. In some implementations, rather than automatically using default values, the treatment manager can prompt the user (e.g., patient and/or caregiver) to provide initial values for the pacing parameters via the user interface. For example, the user interface element may provide a suggested range of values and prompt the user to select from within the range. In some instances, the user may be able to override the default pacing recommendations and provide his or her own preferences for pacing parameters.

In some examples, the user may be prompted to specify an initial discomfort threshold value, which the treatment manager can use to determine the optimum pacing parameters, e.g., using the optimization process described above. In an implementation, the user can change a previously stored baseline and/or default discomfort threshold value, or change any of the baseline and/or default pacing parameter values.

In the act 1602, the one or more pacing pulses may be delivered in conjunction with one or more TENS pulses executed according to a TENS routine associated with the pacing routine 1600. In at least some examples, the TENS pulses are delivered between pacing pulses, e.g., to distract the patient and further reduce the discomfort experienced by the patient during the pacing routine 1600.

In act 1604, the discomfort monitor prompts for, receives, and records discomfort information and records any discomfort information acquired during execution of the pacing pulses for subsequent processing. In some examples, the discomfort information is recorded in the data storage. This discomfort information may be received as voluntary input from the user via the user interface. Examples of discomfort information received via the user interface include utterances (e.g., words, moans, groans, crying, or other expressions) and actuation of a discomfort measuring and/or indicating device (e.g., strain gauge, button, rotary dial, elastic deformable solid). For example, the user can indicate a level of discomfort he or she feels by actuating any of one or more user interface elements as described herein.

In some examples where the discomfort information is received as voluntary input, the discomfort monitor may prompt the user for the input by, for example, presenting a discomfort scale via the user interface. The discomfort scale may include numeric values and the user interface may request that the user rate the discomfort experienced on the numeric scale. The discomfort scale may also include graphical representations (e.g., faces) and the user interface may request that the user rate the discomfort experienced on the graphical scale. In some examples, the discomfort monitor infers the intensity of the discomfort based on the amount of pressure detected by the user interface or the amount of time a user interface element remains actuated. For example, in a manner similar to that outlined above for the baseline process, the voluntary input may be in the form of actuation of one or more user interface elements, such as a force sensor (e.g., piezoelectric, quartz, or ceramic based transducer), a push or squeeze button, a rotary spring-loaded dial, or an elastic deformable solid.

In some examples where the discomfort information is received as voluntary input, the discomfort monitor may prompt the user for a change in input where the input has not changed state for a time period greater than a value of a timeout configurable parameter of the medical device. In this way, these examples prevent involuntary input received as voluntary input from affecting the behavior of the medical device for a time period greater than the timeout.

Also in the act 1604, the discomfort monitor calculates a discomfort parameter that quantifies the discomfort information. This discomfort information quantified by the discomfort monitor may have been voluntary input acquired during execution of the pacing pulses in the act 1602 or may have been received as voluntary input in response to one or more prompts provided to the user via the user interface within the act 1604. In some examples, the discomfort monitor assigns a value to the discomfort parameter based on the discomfort information using one or more of the mechanisms described herein (e.g., the mechanisms described above with reference to the act 408 of FIG. 4). For instance, the discomfort monitor may store any of the following values as the value of the discomfort parameter: a value of a point on the discomfort scale selected via user input, a value calculated based on an amount of pressure exerted by the user on an element of the user interface, or a value calculated based on motion of the patient or some other voluntary action exhibited by the patient and detected by the medical device. For example, the discomfort monitor may cause the medical device to display the value of the discomfort parameter to the user during administration of the pacing routine. As noted above, a user interface may display the discomfort information, for example, in the form of a numerical scale (e.g., 1-10 scale, or percentage scale) or a color coded band of zones.

In act 1606, the discomfort monitor dynamically adjusts the pacing parameters in response to the patient's input. Accordingly, where the patient is conscious and actively contributing discomfort information (e.g., by providing feedback about discomfort substantially in real time and during the administration of the pacing routine), the discomfort monitor determines the adjusted pacing parameters based on a predetermined relationship between the pacing parameters and the discomfort parameter. For instance, where discomfort parameter indicates a conscious patient experiencing a high degree of discomfort, the discomfort monitor may adjust the pacing parameters to deliver no pacing pulses, or only background TENS pulses. Conversely, where the discomfort parameter indicates a conscious patient is experiencing little or no discomfort, and pacing is still required, the discomfort manager may adjust the pacing parameters to deliver pacing pulses with higher efficacy (e.g., by increasing, among other parameters, rate, width, and/or amplitude) in accordance with the principles described herein.

In one example, the range of each pacing parameter within a pacing routine is inversely mapped to a range including all possible values of the discomfort parameter, with lower pacing parameter values corresponding to higher discomfort parameters. In this example, the discomfort manager converts the discomfort parameters to pacing parameters using the inverse map, thereby decreasing pacing parameters (and associated discomfort) in direct portion to the intensity of discomfort reported by the patient.

In act 1608, the treatment manager receives (via the one or more electrodes) and analyzes (via the cardiac monitor) electrode signals generated from detectable characteristics of the patient's cardiac function. During the analysis, the cardiac monitor determines whether the patient's current cardiac condition warrants further pacing. If so, the treatment manager returns to the act 1602 and continues execution of the pacing routine 1600. If the cardiac monitor determines that the patient's current cardiac condition does not warrant further pacing (e.g., determines that a normal sinus rhythm has returned), the pacing routine 1600 ends. In some examples, upon termination of the pacing routine 1600, the treatment manager returns to the process 500 and continues to monitor the patient's physiological signals, such as the patient's ECG, temperature, pulse oxygen level, respiration, etc.

Processes in accord with the managed pacing routine 1600 enable patients to control parameters of pacing routines via immediate feedback provided via a user interface element, thereby enabling patients to actively manage discomfort associated with external pacing processes.

In one example, the patient may not control the pacing (including TENS) parameters individually, but rather controls the degree to which the wearable medical device trades off effectiveness of a pacing routine against discomfort. For instance, the wearable medical device may determine, as a result of the baseline process that the patient responds particularly well to increases in pacing ramp time.

For example, the wearable medical device may determine that the patient is responding well based on a parameter indicating that there are larger changes (system gain) in patient discomfort levels for a particular change in the pacing parameter (e.g., ramp time), and at the same time smaller changes (system gain) in pacing effectiveness for a particular change in the pacing parameter (e.g., ramp time). In some examples, such a parameter can be based on optimizing for either a difference or ratio of these two system gains. For example, such a difference or ratio may be in the form of a "parameter efficiency." These system gains can be estimated in the slopes of the particular parameter on the response surface or the coefficients of the logistic regression or other statistical model.

In one example, the pacing parameters can be changed at the same time in steps for each user request to decrement the pacing discomfort. For example, the step sizes for each parameter can be proportional to a predetermined parameter efficiency. In some cases, the parameter with the highest parameter efficiency can be changed first until there is some loss in pacing capture of the patient, at which point the pacing parameter with the next highest parameter efficiency can be changed in increments. In this manner, the process can be repeated in a predetermined sequence for the remaining parameters.

In some examples, the TENS parameters can be changed in a similar fashion as described above either along with or after other pacing pulse parameters have been set. This results in the changes following along an optimal trajectory along the response surface, minimizing pacing discomfort while maximizing pacing effectiveness.

For example, the response surface may be dynamic depending on the patient's mental or physiologic status or external circumstances. Accordingly, in some embodiments, though the patient may be capable of adjusting the pacing parameters to reduce discomfort, the reduction may be temporary, as a reduction in discomfort may introduce some increase in the level of pacing effectiveness. In one scenario, patient-initiated reduction in discomfort could cause a pacing routine to no longer be effective. As such, if user input is provided by the patient that the discomfort is perceived to be too high, then the discomfort monitor can modify one or more of the pacing parameters to decrease the patient discomfort. Assuming that the original settings provided maximum pacing effectiveness, after a predetermined period of time of e.g., about 5 seconds to 5 minutes, the device can begin to revert all the modified pacing parameters to their original, more effective settings. In this fashion, if the patient loses consciousness because the pacing was ineffectiveness in generating sufficient blood flow, then the device can automatically revert to a life-sustaining (albeit uncomfortable) pacing parameter settings. In some examples, the pacing parameters may be modified in such a fashion that the pacing remains optimally effective during the course of the parameter modifications. In some examples, maintaining optimal effectiveness during the course of parameter modification may take the form of having the parameter changes follow the response surface determined during prior testing and baselining of the patient, or of multiple patients.

In some implementations, the pacing parameter settings may be regulated by a pressure sensitive input, such that, as long as the patient is squeezing the pressure (or force) sensitive input with at least some predetermined threshold level of pressure (or force) then the device will not continue to revert to the original settings.

In some implementations, the pressure sensing may be continuous or substantially continuous, and the patient themselves can autoregulate their pacing parameter settings as described herein.

Fixed Rate and Energy Pacing

In accordance with one example of the act 514, the treatment manager is configured to manage patient discomfort while pacing the heart of a patient at a fixed rate and fixed energy. Fixed rate and energy pacing may be appropriate in response to various types of cardiac arrhythmias. Examples of these types of cardiac arrhythmias include bradycardia, a lack of sensed cardiac activity (spontaneous or post shock asystole), and pulseless electrical activity. In some cases, these cardiac arrhythmias may occur before or after one or more defibrillation shocks. For example, the treatment manager may be configured to provide pulses at a fixed energy level, a fixed pulse width, and a fixed frequency in response to detection of any of the above-noted events via the ECG sensing electrodes. The energy level of the pacing pulses may be set to a fixed value by applying a desired current waveform for a determined duration of time by one or more of the plurality of therapy electrodes.

Figure 6:
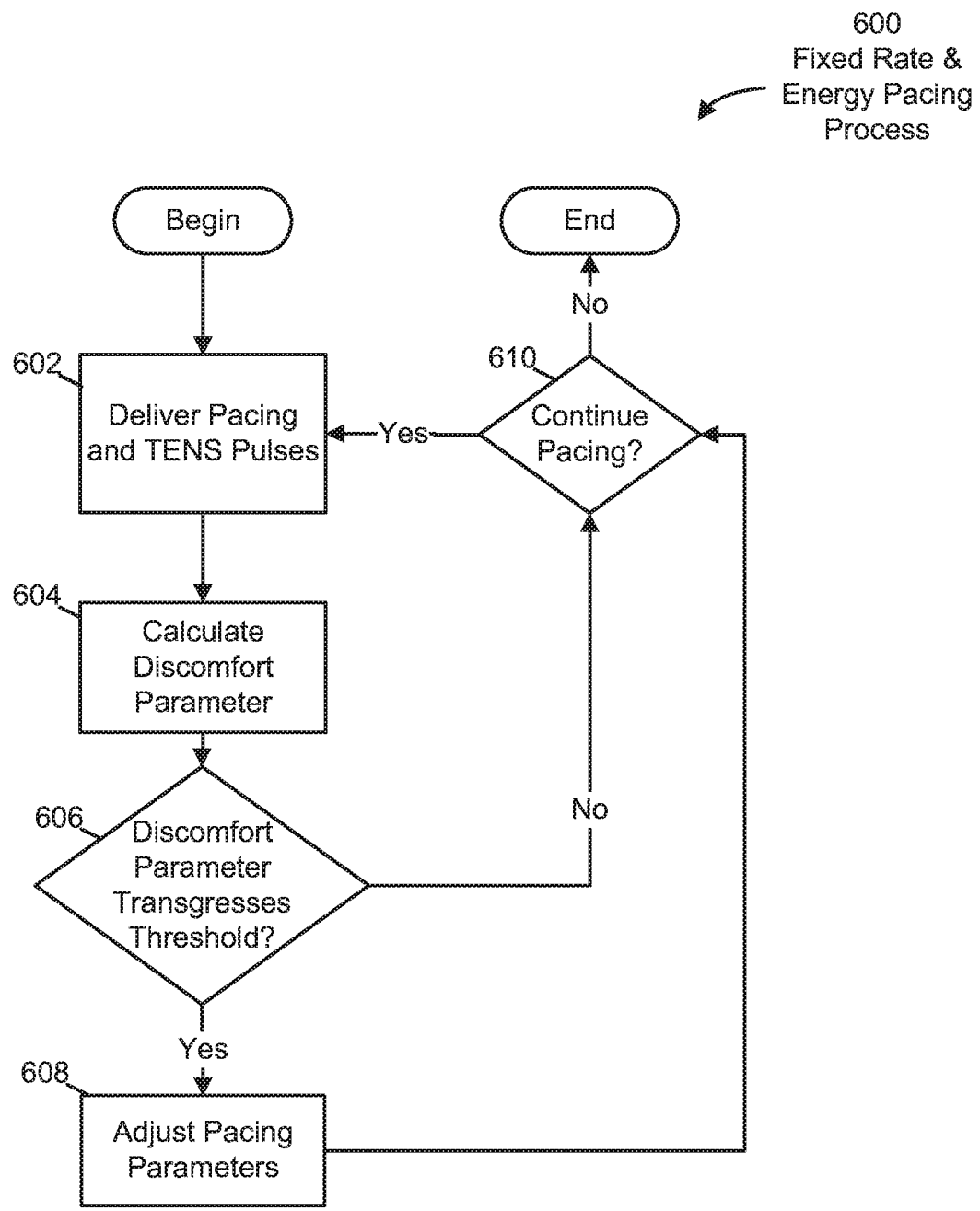
FIG. 6 is a flow diagram of one example managed pacing routine.

FIG. 6 illustrates one example of a managed pacing routine 600 that is executed within the act 514. The managed pacing routine 600 executes a fixed rate and energy pacing process that is managed to decrease discomfort relative to conventional pacing processes. As shown in FIG. 6, the managed pacing routine 600 includes acts of delivering pacing pulses, calculating a discomfort parameter, adjusting pacing parameters, and determining whether pacing should continue.

In act 602, the treatment manager delivers one or more pacing pulses to the patient according to the baseline parameters loaded in the act 512 described above with reference to FIGS. 5 and 16. In examples where the act 512 has been omitted, the treatment manager delivers one or more pacing pulses to the patient in accord with default pacing parameters stored in the data storage. In the act 602, the one or more pacing pulses may delivered in conjunction with one or more TENS pulses executed according to a TENS routine associated with the pacing routine 600.

In act 604, the discomfort monitor prompts for, receives, and records discomfort information and records any discomfort information acquired during execution of the pacing pulses for subsequent processing. In some examples, the discomfort information is recorded in the data storage. This discomfort information may be received as voluntary or involuntary input from the user via the user interface or may be acquired from one or more other sensors coupled to a sensor interface. Examples of discomfort information received via the user interface include utterances (e.g., words, moans, groans, crying, or other expressions) and actuation of a discomfort measuring and/or indicating device (e.g., strain gauge, button, rotary dial, elastic deformable solid). For example, the user can indicate a level of discomfort he or she feels by actuating any of one or more user interface elements as described herein. Examples of discomfort information received via other sensors (e.g., motion detection sensors, strain gauges in a garment) include movements (e.g., tensing of muscles, jerking, shuttering, flinching, changes in respiration) and lack of movement.

In some examples where the discomfort information is received as voluntary input, the discomfort monitor may prompt the user for the input by, for example, presenting a discomfort scale via the user interface. The discomfort scale may include numeric values and the user interface may request that the user rate the discomfort experienced on the numeric scale. The discomfort scale may also include graphical representations (e.g., faces) and the user interface may request that the user rate the discomfort experienced on the graphical scale. In some examples, the discomfort monitor infers the intensity of the discomfort based on the amount of pressure detected by the user interface or the amount of time a user interface element remains actuated. For example, in a manner similar to that outlined above for the baseline process, the voluntary input may be in the form of actuation of one or more user interface elements, such as a force sensor (e.g., piezoelectric, quartz, or ceramic based transducer), a push or squeeze button, a rotary spring-loaded dial, or an elastic deformable solid.

In some examples where the discomfort information is received as voluntary input, the discomfort monitor may prompt the user for a change in input where the input has not changed state for a time period greater than a value of a timeout configurable parameter of the medical device. In this way, these examples prevent involuntary input received as voluntary input from affecting the behavior of the medical device for a time period greater than the timeout.

In the act 606, the discomfort monitor determines whether the pacing pulses delivered in the previous iteration of the act 602 were tolerable to the patient based on any of the mechanisms described herein. If the pacing pulses were tolerable, the treatment manager proceeds to the act 610. If the pacing pulses were not tolerable, the treatment manager proceeds to the act 608. In some examples, the discomfort monitor determines whether the pacing pulses were tolerable at least in part by quantifying discomfort information. This discomfort information quantified by the discomfort monitor may have been acquired during execution of the pacing pulses in the act 602 or may have been received as voluntary input in response to one or more prompts provided to the user via the user interface within the act 604 (i.e., after execution of the pacing pulses in act 602 is complete). In some examples, the discomfort monitor assigns a value to the discomfort parameter based on the discomfort information using one or more of the mechanisms described herein (e.g., the mechanisms described above with reference to the act 408 of FIG. 4). For instance, the discomfort monitor may store any of the following values as the value of the discomfort parameter: a value of a point on the discomfort scale selected via user input, a value calculated based on an amount of pressure exerted by the user on an element of the user interface, or a value calculated based on motion of the patient or some other involuntary reaction to the pacing pulses exhibited by the patient.

In some examples, the discomfort monitor determines whether the pacing pulses were tolerable by comparing the value of the discomfort parameter to a discomfort threshold value. This discomfort threshold value may be a configurable parameter of the medical device. In some examples, the discomfort monitor determines that the pacing pulses were tolerable where the value of the discomfort parameter maintains a predefined relationship with to the discomfort threshold value (e.g., where the value of the discomfort parameter does not transgress the discomfort threshold value). In these examples, the discomfort monitor determines that the pacing pulses were not tolerable where the value of the discomfort parameter does not maintain a predefined relationship with the discomfort threshold value (e.g. where the value of the discomfort parameter is equal to or transgresses the discomfort threshold value). It is appreciated that, depending on the specific calculations used, a discomfort threshold value may be transgressed by a value that is greater than or less than the discomfort threshold value.

In act 608, the discomfort monitor adjusts the pacing parameters. In some examples, the discomfort monitor determines the adjusted pacing parameters substantially in real time based on immediate feedback from the patient as described above with reference to FIG. 16.

In some examples, where voluntary feedback is unavailable (e.g., the patient is unable to provide dynamic feedback regarding his or her level of discomfort) the discomfort monitor determines the adjusted pacing parameters in a similar manner as outlined above with respect to the baseline process 400 by solving an optimization problem similar to the optimization problem described above with reference to described above with reference to act 412 of FIG. 4. However, the optimization problem solved within the act 608 replaces these constraints:

15 milliamps≤$a_i$≤200 milliamps;

0.5 milliseconds≤$w_i$≤40 milliseconds; and 20 pacing pulses per minute≤$r_i$≤200 pacing pulses per minute with the following constraints:

$a_i=a_b$ (or the value of a configurable parameter set for fixed energy and rate pacing);

$w_i=w_b$ (or the value of a configurable parameter set for fixed energy and rate pacing); and $r_i=r_b$ (or the value of a configurable parameter set for fixed energy and rate pacing). In addition, the discomfort monitor improves any approximation of the function d(i) by incorporating the data point(s) generated in act 606.

In act 610, the treatment manager receives (via the one or more electrodes) and analyzes (via the cardiac monitor) electrode signals generated from detectable characteristics of the patient's cardiac function. The cardiac monitor determines whether the patient's current cardiac condition warrants further pacing. If so, the treatment manager returns to the act 602 and continues execution of the pacing routine 600. If the cardiac monitor determines that the patient's current cardiac condition does not warrant further pacing (e.g., determines whether a normal sinus rhythm has returned), the pacing routine 600 ends. In some examples, upon termination of the pacing routine 600, the treatment manager returns to the process 500 and continues to monitor the patient's physiological signals, such as the patient's ECG, temperature, pulse oxygen level, respiration, etc.

During an initial fitting of a medical device that may execute the fixed rate and energy pacing routine 600, the level of current (pulse amplitude), the pulse width, and the frequency (rate) of the pulses may be set to an appropriate level based on the input of a medical professional (such as the patient's cardiologist) and the physiological condition of the patient (e.g., based on the patient's normal resting heart rate, the patient's thoracic impedance, etc.) In some examples, the level of current, the pulse width, and the frequency of the pulses may simply be set to an appropriate value based on typical impedance values for an adult or child, and typical resting heart rates for an adult or child. This initial fitting may be performed in accord with the act 402 described above with reference to FIG. 4 or otherwise.

It should be appreciated that because pacing at a fixed rate may interfere with the patient's own intrinsic heart rate, the treatment manager can be configured to perform such fixed rate and energy pacing only in the event of a life-threatening bradycardia, a lack of any detected cardiac activity following shock, or in response to pulseless electrical activity following a shock.

Processes in accord with the managed pacing routine 600 enable patients to control parameters of pacing routines via feedback provided to a user interface, thereby enabling patients to actively manage discomfort associated with external pacing processes.

Demand (Adjustable Rate) Pacing

In accordance with one example of the act 514, the treatment manager is configured to manage patient discomfort while pacing the heart of a patient at a variable rate and a fixed energy. Variable rate and fixed energy pacing may be appropriate in response to various types of cardiac arrhythmias, including a bradycardia (i.e., an excessively slow heart rate below 40 beats per minute), tachycardia (i.e., an excessively fast heart rate), an erratic heart rate with no discernible regular sinus rhythm, a lack of sensed cardiac activity (asystole), and pulseless electrical activity. Some of these cardiac arrhythmias may occur following one or more defibrillation shocks.

As known to those skilled in the art, pacing at a fixed rate and energy may not be appropriate for the particular type of cardiac arrhythmia of the patient, and even where the rate and energy level are appropriate, pacing at a fixed rate can result in competition between the rate at which the pacing pulses are being applied and the intrinsic rhythm of the patient's heart. For example, pacing at a fixed rate may result in the application of a pacing pulse during the relative refractory period of the normal cardiac cycle (a type of R wave on a T wave effect) that could promote ventricular tachycardia or ventricular fibrillation. To overcome some of the disadvantages of fixed rate and energy pacing, the treatment manager can be configured to perform demand pacing, wherein the rate of the pacing pulses may be varied dependent on the physiological state of the patient and the patient's current discomfort parameter. For example, during demand pacing, the treatment manager can deliver a pacing pulse only when needed by the patient. In general, when executing in demand mode, the device searches for any intrinsic cardiac activity of the patient, and if a heartbeat is not detected within a designated interval, a pacing pulse is delivered and a timer is set to the designated interval. Where the designated interval expires without any detected intrinsic cardiac activity of the patient, another pacing pulse is delivered and the timer reset. In some examples, where an intrinsic heartbeat of the patient is detected within the designated interval, the device resets the timer and continues to search for intrinsic cardiac activity.

Figure 9:
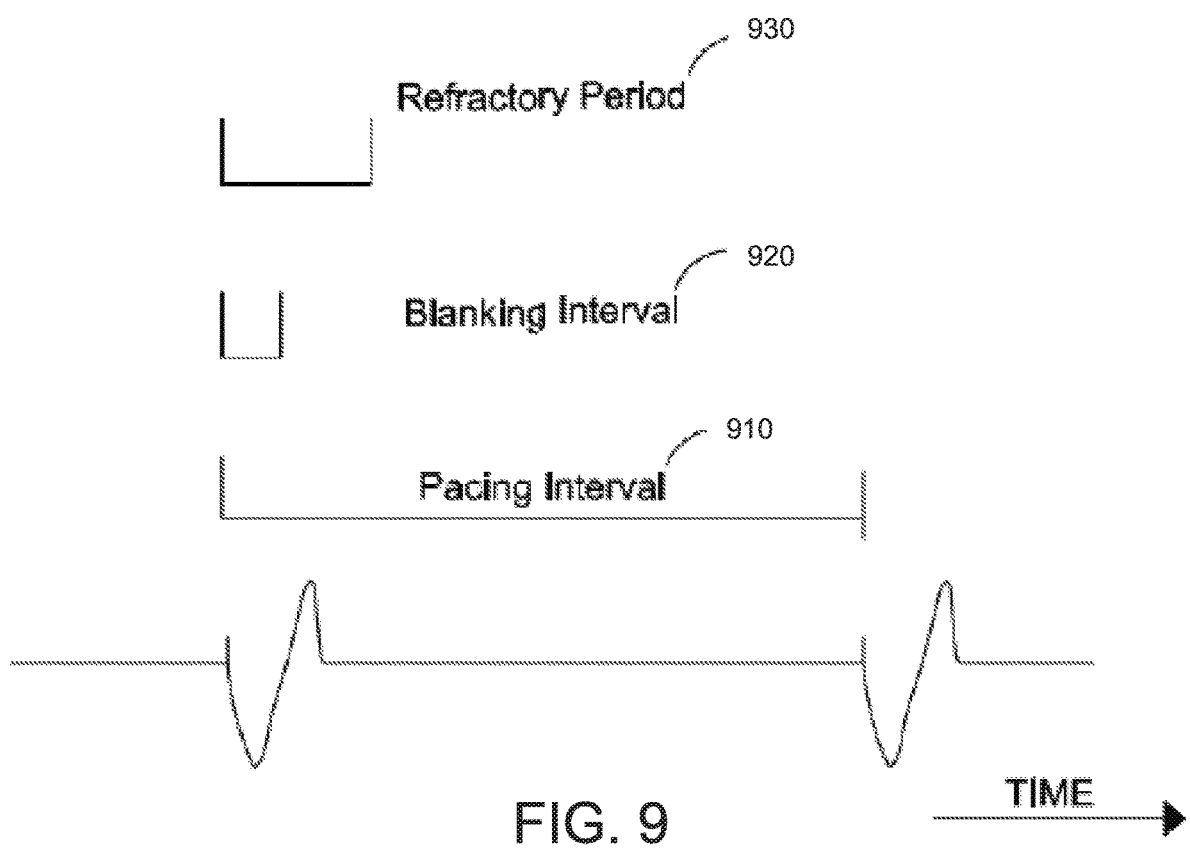
FIG. 9 is a graph illustrating various aspects of demand pacing which can be adjusted in connection with on demand pacing or capture management pacing.
Figure 10:
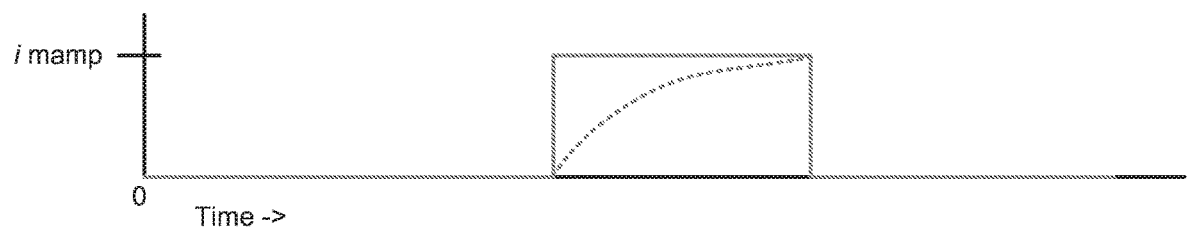
FIG. 10 is a graph illustrating a pacing waveform that may be provided by the medical monitoring and treatment device.
Figure 11:
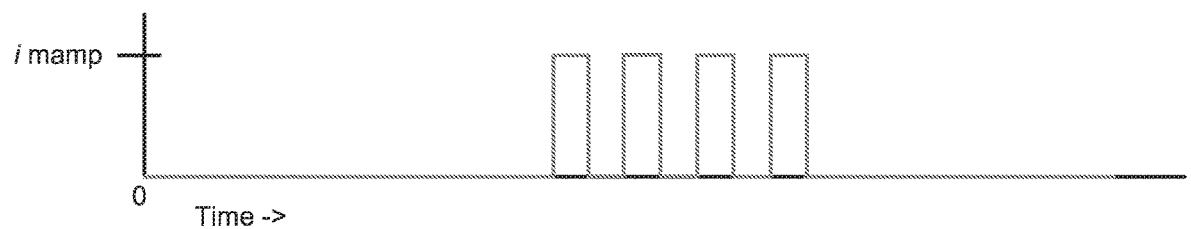
FIG. 11 is a graph illustrating another pacing waveform that may be provided by the medical monitoring and treatment device.
Figure 12:
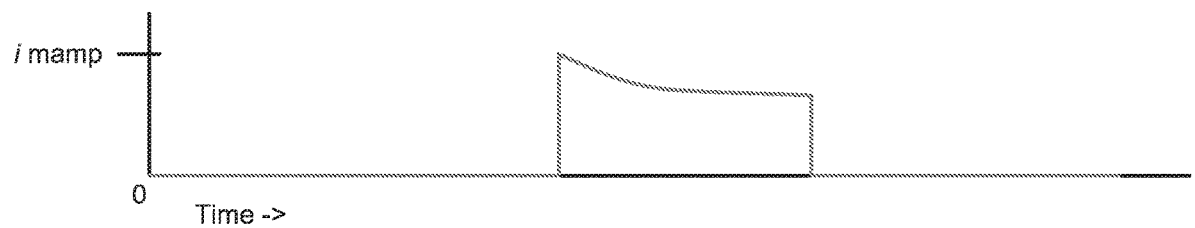
FIG. 12 is a graph illustrating another pacing waveform that may be provided by the medical monitoring and treatment device.
Figure 13:
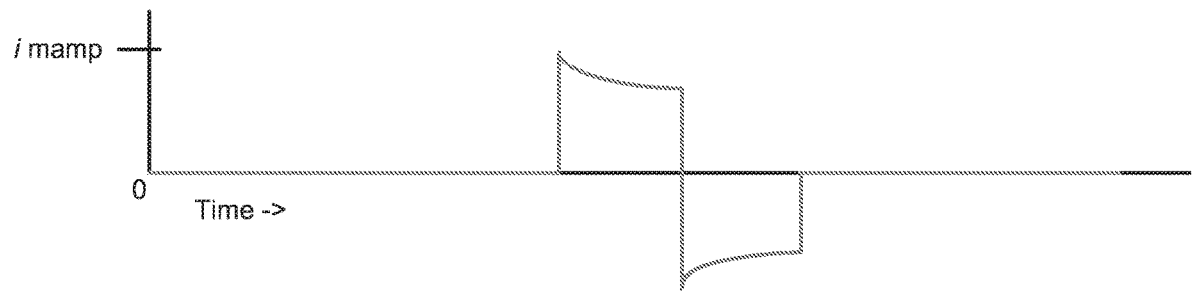
FIG. 13 is a graph illustrating another pacing waveform that may be provided by the medical monitoring and treatment device.
Figure 14:
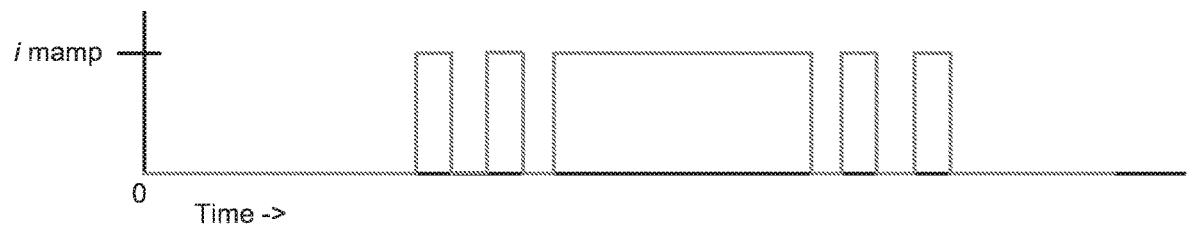
FIG. 14 is a graph illustrating another pacing waveform that may be provided by the medical monitoring and treatment device.
Figure 15:
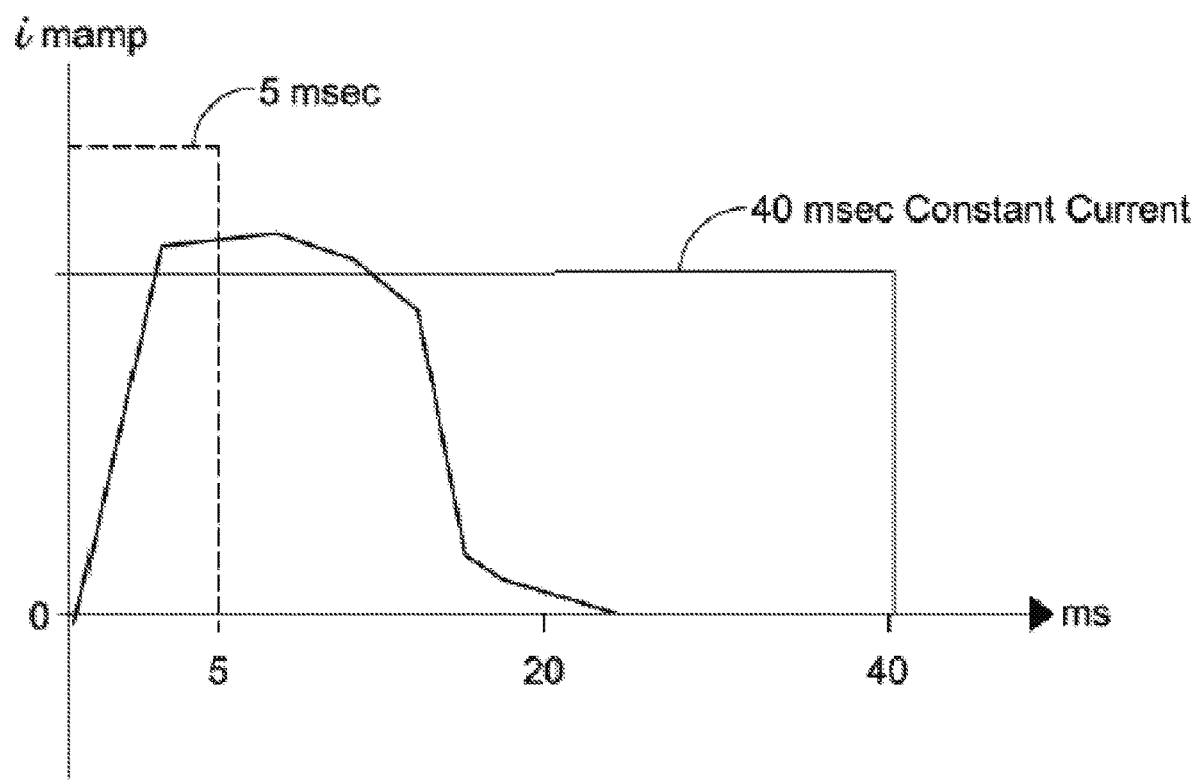
FIG. 15 is a graph illustrating a number of different pacing waveforms that may be provided by the medical monitoring and treatment device, including a 40 ms constant current pulse.

FIG. 9 helps to illustrate some of the aspects of demand pacing and the manner in which demand pacing can be performed by the treatment manager. As illustrated in FIG. 9, when executing demand pacing, the treatment manager may have a variable pacing interval 910 corresponding to the rate at which pacing pulses are delivered to the patient in the absence of any intrinsic cardiac activity as may be detected by the cardiac monitor. For example, the rate at which pulsing paces are to be delivered to the patient (referred to as the "base pacing rate" herein) may be set at 60 pulses per minute and therefore, the corresponding base pacing interval 910 would be set to 1 second.

Although the base pacing rate may be set to a particular value based on the physiological condition of the patient and input from a medical professional, the treatment manager can include a number of different pacing routines to respond to different cardiac arrhythmias, such as bradycardia, tachycardia, an erratic heart rate with no discernible regular sinus rhythm, asystole, or pulseless electrical activity. These pacing routines may be implemented using a variety of hardware and software components and examples are not limited to a particular configuration of hardware or software. For instance, the pacing routines may be implemented using an application-specific integrated circuit (ASIC) tailored to perform the functions described herein.

The treatment manager may also have a hysteresis rate (not shown in FIG. 9) corresponding to the detected intrinsic heart rate of the patient below which the device performs pacing. According to some examples, the hysteresis rate is a configurable parameter that is expressed as a percentage of the patient's intrinsic heart rate. In the above example, the hysteresis rate may correspond to 50 beats per minute. In this example, if the intrinsic heart rate of the patient fell to 50 beats per minute or below (e.g., more than approximately 1.2 seconds between detected beats), the treatment manager would generate and apply a pacing pulse to the patient.

During application of a pacing pulse to the body of a patient and a short time thereafter, the treatment manager may intentionally blank out a portion of the ECG signals being received by the ECG monitoring and detection circuitry (e.g., the electrodes, sensor interface, and cardiac monitor) to prevent this circuitry, which may include amplifiers, A/D converters, etc. from being overwhelmed (e.g., saturated) by the pacing pulse. This may be performed in hardware, software, or a combination of both. This period of time, referred to herein as "the blanking interval" 920 may vary (e.g., between approximately 30 milliseconds to 200 milliseconds), but is typically between approximately 40 milliseconds to 80 milliseconds in duration.

In addition to the blanking interval 920, the treatment manager can have a variable refractory period 930 that may vary dependent upon the base pacing rate. The refractory period 930 corresponds to a period of time in which signals sensed by the ECG sensing electrodes are ignored, and may include the blanking interval. The refractory period 930 allows any generated QRS complexes or T waves induced in the patient by virtue of the pacing pulse to be ignored, and not interpreted as intrinsic cardiac activity of the patient. The refractory period can be configured as is done with VVI implanted pacemakers, e.g., with a single chamber, ventricular sensed, ventricular stimulation pacemakers known to those skilled in the art. For example, the refractory period can be an interval following a paced or sensed event in the chamber containing the pacing or sensing lead, during which the inhibited (SSI) or triggered (SST) pacemaker is not reset. In a VVI pacemaker, a first part of the refractory period is a programmable, absolutely refractory blanking period. For example, it prevents a resetting of the pacemaker by a sensing of a) post-pacing ventricular potentials, b) the end of the QRS, or c) the T wave. For example, an occurrence of an event during the blanking period may not be visible on the marker channels. For typical applications, the refractory period is generally between about 150 milliseconds and 400 milliseconds.

In one example, the sensitivity of the ECG monitoring and detection that is performed by the treatment manager may also be varied to adjust the degree by which the ECG monitoring and detection circuitry can detect the patient's intrinsic cardiac activity. For example, where the amplitude of certain discernible portions (e.g., an R-wave) of a patient's intrinsic ECG signal is below that typically encountered, the voltage threshold over which this discernible portion can be detected as belonging to an ECG signal (and not attributed to noise or other factors) may be lowered, for example from 2.5 millivolts to 1.5 millivolts, to better detect the patient's intrinsic cardiac activity. For instance, during an initial fitting of the medical device, the sensitivity threshold of the device may be reduced to a minimal value (e.g., 0.4 millivolts) and the patient's intrinsic ECG signals may be monitored. The sensitivity threshold may then be incrementally increased (thereby decreasing the sensitivity of the device) and the patient's intrinsic ECG signals monitored until these ECG signals are no longer sensed. The sensitivity threshold may then be incrementally decreased (thereby increasing the sensitivity of the device) until the patient's intrinsic ECG signals are again sensed, and the sensitivity threshold of the device may be set to approximately half this value.

As with fixed energy and rate pacing, the treatment manager may be configured during an initial fitting per the act 402 or otherwise to provide pulses at a fixed energy level and a fixed pulse width in response to detection of any of the above-noted events by the cardiac monitor. The maximum current level of the current waveform may be set to a value between approximately 10 milliamps to 200 milliamps, the pulse width may be set to a fixed value between approximately 20 milliseconds to 40 milliseconds, and the base rate of the pulses may be set to a fixed value between approximately 30 pulses per minute to approximately 200 pulses per minute, although the actual rate of the pacing pulses can vary based upon the intrinsic cardiac activity of the patient. In accordance with one example, a 40 millisecond constant current pulse is used, and the current level is set to a fixed value based upon the input of a medical professional, such as the patient's cardiologist and the physiological condition of the patient. The base pacing rate and the hysteresis rate may also be set based upon the input of the patient's cardiologist (or other medical professional) and the physiological condition of the patient, and the blanking interval and refractory period set to an appropriate time interval based upon the base pacing rate and/or the hysteresis rate.

Figure 7:
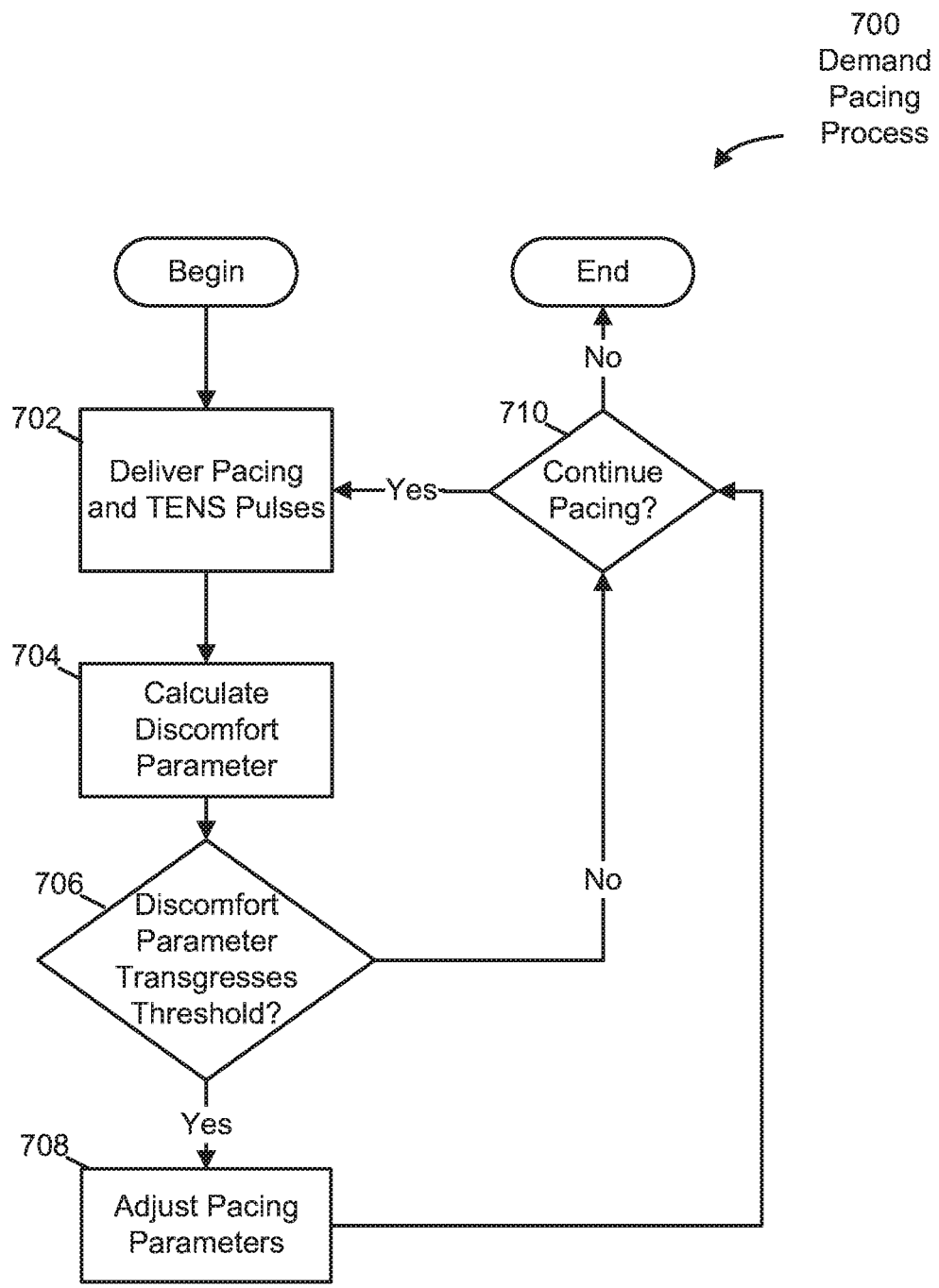
FIG. 7 is a flow diagram of one example managed pacing routine.

FIG. 7 illustrates one example of a managed pacing routine 700 that is executed within the act 514. The managed pacing routine 700 executes a variable rate and fixed energy pacing process that is managed to decrease discomfort relative to conventional pacing processes. As shown in FIG. 7, the managed pacing routine 700 includes acts of delivering pacing pulses, calculating a discomfort parameter, adjusting pacing parameters, and determining whether pacing should continue.

In act 702, the treatment manager delivers one or more pacing pulses to the patient according to the baseline parameters loaded in the act 512 described above with reference to FIG. 5. In examples where the act 512 has been omitted, the treatment manager delivers one or more pacing pulses to the patient in accord with default pacing parameters stored in the data storage. In the act 702, the one or more pacing pulses may be delivered in conjunction with one or more TENS pulses executed according to a TENS routine associated with the pacing routine 700.

In act 704, the discomfort monitor prompts for, receives, and records discomfort information and records any discomfort information acquired during execution of the pacing pulses for subsequent processing. In some examples, the discomfort information is recorded in the data storage. This discomfort information may be received as voluntary or involuntary input from the user via the user interface or may be acquired from one or more other sensors coupled to a sensor interface. Examples of discomfort information received via the user interface include utterances (e.g., words, moans, groans, crying, or other expressions) and actuation of a discomfort measuring and/or indicating device (e.g., strain gauge, button, rotary dial, elastic deformable solid). For example, the user can indicate a level of discomfort he or she feels by actuating any of one or more user interface elements as described herein. Examples of discomfort information received via other sensors (e.g., motion detection sensors, strain gauges in a garment) include movements (e.g., tensing of muscles, jerking, shuttering, flinching, changes in respiration) and lack of movement.

In some examples where the discomfort information is received as voluntary input, the discomfort monitor may prompt the user for the input by, for example, presenting a discomfort scale via the user interface. The discomfort scale may include numeric values and the user interface may request that the user rate the discomfort experienced on the numeric scale. The discomfort scale may also include graphical representations (e.g., faces) and the user interface may request that the user rate the discomfort experienced on the graphical scale. In some examples, the discomfort monitor infers the intensity of the discomfort based on the amount of pressure detected by the user interface or the amount of time a user interface element remains actuated. For example, in a manner similar to that outlined above for the baseline process, the voluntary input may be in the form of actuation of one or more user interface elements, such as a force sensor (e.g., piezoelectric, quartz, or ceramic based transducer), a push or squeeze button, a rotary spring-loaded dial, or an elastic deformable solid.

In some examples where the discomfort information is received as voluntary input, the discomfort monitor may prompt the user for a change in input where the input has not changed state for a time period greater than a value of a timeout configurable parameter of the medical device. In this way, these examples prevent involuntary input received as voluntary input from affecting the behavior of the medical device for a time period greater than the timeout.

In the act 706, the discomfort monitor determines whether the pacing pulses delivered in the previous iteration of the act 702 were tolerable to the patient. If the pacing pulses were tolerable, the treatment manager proceeds to the act 710. If the pacing pulses were not tolerable, the treatment manager proceeds to the act 708. In some examples, the discomfort monitor determines whether the pacing pulses were tolerable at least in part by quantifying discomfort information. This discomfort information quantified by the discomfort monitor may have been acquired during execution of the pacing pulses in the act 702 or may have been received as voluntary input in response to one or more prompts provided to the user via the user interface within the act 704 (i.e., after execution of the pacing pulses in act 702 is complete). In some examples, the discomfort monitor assigns a value to the discomfort parameter based on the discomfort information using one or more of the mechanisms described herein (e.g., the mechanisms described above with reference to the act 408 of FIG. 4). For instance, the discomfort monitor may store any of the following values as the value of the discomfort parameter: a value of a point on the discomfort scale selected via user input, a value calculated based on an amount of pressure exerted by the user on an element of the user interface, or a value calculated based on motion of the patient or some other involuntary reaction to the pacing pulses exhibited by the patient.

In some examples, the discomfort monitor determines whether the pacing pulses were tolerable by comparing the value of the discomfort parameter to a discomfort threshold value. This discomfort threshold value may be a configurable parameter of the medical device. In some examples, the discomfort monitor determines that the pacing pulses were tolerable where the value of the discomfort parameter maintains a predefined relationship with to the discomfort threshold value (e.g., where the value of the discomfort parameter does not transgress the discomfort threshold value). In these examples, the discomfort monitor determines that the pacing pulses were not tolerable where the value of the discomfort parameter does not maintain a predefined relationship with the discomfort threshold value (e.g. where the value of the discomfort parameter is equal to or transgresses the discomfort threshold value). It is appreciated that, depending on the specific calculations used, a discomfort threshold value may be transgressed by a value that is greater than or less than the discomfort threshold value.

In act 708, the discomfort monitor adjusts the pacing parameters. In some examples, the discomfort monitor determines the adjusted pacing parameters substantially in real time based on immediate feedback from the patient as described above with reference to FIG. 16.

In some examples, where voluntary feedback is unavailable (e.g., the patient is unable to provide dynamic feedback regarding his or her level of discomfort) the discomfort monitor determines the adjusted pacing parameters in a similar manner as outlined above with respect to the baseline process 400 by solving an optimization problem similar to the optimization problem described above with reference to described above with reference to act 412 of FIG. 4. However, the optimization problem solved within the act 708 replaces the these constraints:

15 milliamps≤$a_i$≤200 milliamps;

0.5 milliseconds≤$w_i$≤40 milliseconds; and 20 pacing pulses per minute≤$r_i$≤200 pacing pulses per minute; with the following constraints:

$a_i = a_b$ (or the value of a configurable parameter set for demand pacing);

$w_i = w_b$ (or the value of a configurable parameter set for demand pacing); and $r_i$≥hysteresis rate. In addition, the discomfort monitor improves any approximation of the function d(i) by incorporating the data point(s) generated in act 706.

In act 710, the treatment manager receives (via the one or more electrodes) and analyzes (via the cardiac monitor) electrode signals generated from detectable characteristics of the patient's cardiac function. The cardiac monitor determines whether the patient's current cardiac condition warrants further pacing. If so, the treatment manager returns to the act 702 and continues execution of the pacing routine 700. If the cardiac monitor determines that the patient's current cardiac condition does not warrant further pacing (e.g., determines whether a normal sinus rhythm has returned), the pacing routine 700 ends. In some examples, upon termination of the pacing routine 700, the treatment manager returns to the process 500 and continues to monitor the patient's physiological signals, such as the patient's ECG, temperature, pulse oxygen level, respiration, etc.

Processes in accord with the managed pacing routine 700 enable patients to control parameters of pacing routines via feedback provided to a user interface, thereby enabling patients to actively manage discomfort associated with external pacing processes.

Demand Pacing—Bradycardia

As discussed above, where bradycardia is detected and the intrinsic cardiac rate of the patient is below that of the hysteresis rate, the treatment manager will pace the patient at the pre-set base pacing rate and manage the patient's discomfort by executing the pacing routine process 700. During this time, the device will continue to monitor the patient's intrinsic heart rate and will withhold pacing pulses in the event that an intrinsic heartbeat is detected within designated interval corresponding to the hysteresis rate. This type of on demand pacing is frequently termed "maintenance pacing."

Demand Pacing—Tachycardia

For responding to tachycardia, the treatment manager may additionally include another pacing rate, referred to as an "anti-tachyarrhythmic pacing rate" herein, above which the treatment manager will identify that the patient is suffering from tachycardia, and will pace the patient in a manner to bring the patient's intrinsic heart back toward the base pacing rate and manage the patient's discomfort by executing the pacing routine process 700. For example, the treatment manager may employ a technique known as overdrive pacing wherein a series of pacing pulses (e.g., between about 5 and 10 pacing pulses) are delivered to the patient at a rate above the intrinsic rate of the patient in an effort to gain control of the patient's heart rate. Once it is determined that the treatment manager is in control of the patient's heart rate, the rate of the pulses may be decremented, for example by about 10 milliseconds, and another series of pacing pulses delivered. This delivery of pulses and the decrease in frequency may continue until the detected intrinsic cardiac rate of the patient is below the anti-tachyarrhythmic pacing rate. This type of pacing is frequently termed "overdrive pacing" or "fast pacing."

Demand Pacing—Erratic Heart Rate

For responding to an erratic heart rate, the treatment manager may perform a type of pacing that is similar to a combination of maintenance pacing and overdrive pacing discussed above. For example, where the treatment manager detects an erratic heart rate with no discernible sinus rhythm, the treatment manager may deliver a series of pacing pulses (e.g., between about 5 and 10 pacing pulses) to the patient at a particular rate, while managing the patient's discomfort in accord with the pacing routine 700. This rate may be one that is above a lower rate of a series of detected intrinsic beats of the patient's heart and below an upper rate of the detected intrinsic beats of the patient's heart. After delivering the series of pulses, the treatment manager may monitor the patient's heart to determine if it has synchronized to the rate of the series of delivered pulses. Where the intrinsic rate of the patient's heart is still erratic, the treatment manager may increase the rate of the series of pulses and deliver another series. This may continue until it is established that the patient's heart assumes a more regular state. Upon determining that the patient's heart is in a more regular state, the treatment manager may perform maintenance pacing if it is determined that the patient's intrinsic heart rate is too low as discussed in the "Demand Pacing—Bradycardia" section above, or perform pacing at a decremented rate in the manner discussed in "Demand Pacing—Tachycardia" section above, if such is warranted.

Demand Pacing—Asystole or Pulseless Electrical Activity

For responding to asystole or a detected condition of pulseless electrical activity, the treatment manager may perform maintenance pacing similar to that described in the "Demand Pacing—Bradycardia" section above and manage patient discomfort by executing the pacing routine 700. This type of pacing would be performed after a series of one or more defibrillating shocks that attempt to restore a normal sinus rhythm to the heart of the patient.

In each of the types of pacing described above, the treatment manager may be configured to perform a particular type of pacing only after a programmable delay after such cardiac arrhythmias are detected, or after a programmable period of time after one or more defibrillating shocks are delivered.

Capture Management

In one example of the act 514, the treatment manager is configured to manage patient discomfort while pacing the heart of a patient using capture management with an adjustable energy level and an adjustable rate in response to various types of cardiac arrhythmias. The various types of cardiac arrhythmias can include a bradycardia, tachycardia, an erratic heart rate with no discernible regular sinus rhythm, a lack of sensed cardiac activity (asystole) following or independent of one or more defibrillation shocks, a life-threatening bradycardia following one or more defibrillation shocks, or pulseless electrical activity following one or more defibrillation shocks.

As known to those skilled in the art, capture management refers to a type of pacing in which the energy level of pacing pulses and the rate of delivery of those pacing pulses may be varied based upon the detected intrinsic activity level of the patient's heart and the detected response of the patient's heart to those pacing pulses. In cardiac pacing, the term "capture" is used to refer to the response of a patient's heart to a pulse of energy which results in ventricular depolarization. In cardiac pacing, it is desirable to limit the amount of energy in each pulse to a minimal amount required for capture; thereby decreasing the amount of discomfort associated with external pacing.

In general, the manner in which the treatment manager performs capture management pacing is similar to that of demand pacing described above, in that it may adjust the rate at which pacing pulses are delivered based upon the detected intrinsic rate of cardiac activity of the patient and, potentially, based on the a level of discomfort being experienced by the patient. The sensitivity of the device to the patient's ECG may be adjusted in a similar manner to that described above with respect to demand pacing. Further, capture management pacing may be used to treat the same types of cardiac arrhythmias as the demand pacing described above, such as bradycardia, tachycardia, an erratic heart rate with no discernible sinus rhythm, asystole, or pulseless electrical activity.

However, in contrast to a medical device that performs demand pacing, a medical device that is configured to perform capture management pacing will typically have a refractory period 930 (see FIG. 9) that is significantly shorter than a device configured to perform demand pacing. Indeed, when using capture management pacing, there may be no refractory period 930 at all, but only a blanking interval 920. In some examples, where there is a refractory period 930, the refractory period 930 may be similar in duration to the blanking interval 920. As would be appreciated by those skilled in the art, this is because during capture management pacing, the response of the patient's heart is monitored to detect whether the delivered pulse of energy resulted in capture.

During capture management pacing, the treatment manager can initially deliver a pulse of energy at a predetermined, low energy level and monitor the patient's response to determine if capture resulted. Where it is determined that the delivered pulse did not result in capture, the energy level of the next pulse may be increased. For example, where the treatment manager resides in a medical device that is external to the patient, the initial setting may be configured to provide a 40 milliseconds rectilinear and constant current pulse of energy at a current of 40 milliamps, and increase the amount of current in increments of 2 milliamps until capture results. The next pacing pulse may be delivered at increased current relative to the first pacing pulse and at a desired rate relative to the first pacing pulse in the absence of any detected intrinsic cardiac activity of the patient or intolerable discomfort to the patient. Where the next pacing pulse does not result in capture, the energy may be increased until capture is detected. The treatment manager may then continue pacing at this energy level and at a desired rate in the absence of any detected intrinsic cardiac activity of the patient or intolerable discomfort to the patient. During this period of time, the treatment manager monitors the patient's cardiac response to the pacing pulses, and may increment the energy level further, should it be determined over one or more subsequent pulses that capture did not result. Similarly, during this period, the discomfort monitor tracks the patient's discomfort parameter and may adjust one or more pacing parameters in response to determining that the patient's discomfort parameter has, for example, transgressed a discomfort threshold value.

In one example, the treatment manager may apply a series of pulses at an initial energy level and rate, and monitor the patient's response to determine if capture resulted. Where capture did not result, or where capture resulted in response to some of the pulses, but not all, the treatment manager may increase the energy of a next series of pulses until capture results for each pulse.

In some examples, the treatment manager may be configured to identify a minimum amount of energy that results in capture during capture management pacing. Where it is determined that the delivered pulse did result in capture, the energy level of the next pulse may be decreased. For example, where the treatment manager resides in a medical device that is external to the patient, the initial setting may be configured to provide a 40 milliseconds constant current pulse of energy at a current of 70 milliamps. Where it is determined that the delivered pulse resulted in capture, subsequent pacing pulse may be delivered at decreased in increments of 5 milliamps (or more where the discomfort parameter value exceeds the discomfort threshold value) and at a desired rate relative to the first pacing pulse in the absence of any detected intrinsic cardiac activity of the patient until capture is no longer achieved or until the discomfort parameter of the patient transgress the discomfort threshold value. Where the next pacing pulse does not result in capture, the energy setting may be increased to the last current known to produce a pulse resulting in capture, and then delivering a pulse at the higher energy setting, thus delivering the minimal amount of energy required for capture. The treatment manager may then continue pacing at this energy level and at a desired rate in the absence of any detected intrinsic cardiac activity of the patient or intolerable discomfort to the patient. During this period of time, a similar routine may be re-performed at predetermined intervals to ensure that the minimum amount of energy is being delivered for capture. In addition, during this period of time, the treatment manager monitors the patient's cardiac response to the pacing pulses, and may increase the energy level should it be determined over one or more subsequent pulses that capture did not result.

Figure 8:
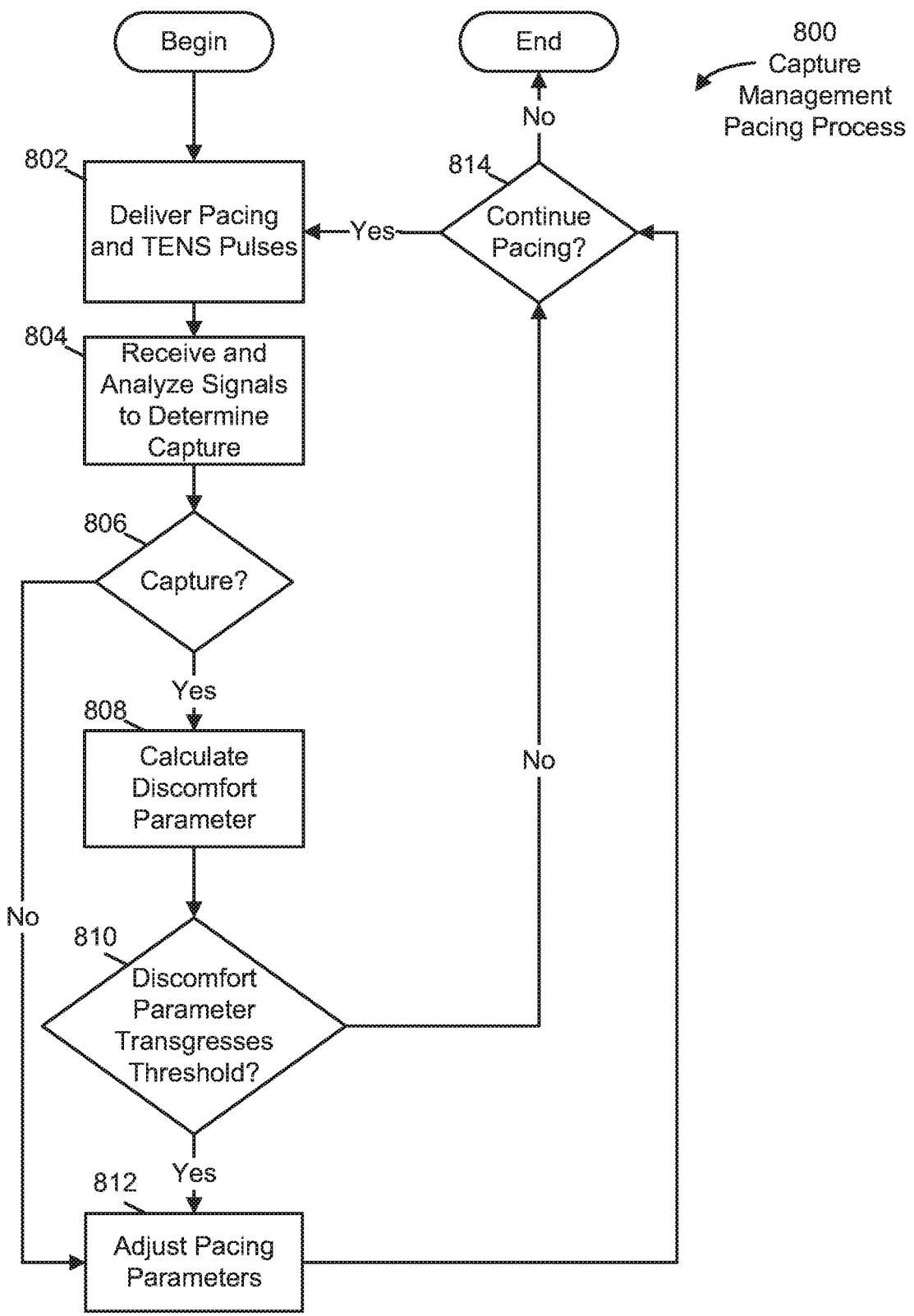
FIG. 8 is a flow diagram of one example managed pacing routine.

FIG. 8 illustrates one example of a managed pacing routine 800 that is executed within the act 514. The managed pacing routine 800 executes a capture management pacing process that is managed to decrease discomfort relative to conventional pacing processes. As shown in FIG. 8, the managed pacing routine 800 includes acts of delivering pacing pulses, receiving and analyzing ECG signals, determining whether capture occurred, calculating a discomfort parameter, determining whether the discomfort caused by the pacing routine 800 is intolerable, adjusting pacing parameters, and determining whether pacing should continue.

In act 802, the treatment manager delivers one or more pacing pulses to the patient according to the baseline parameters loaded in the act 512 described above with reference to FIG. 5. In examples where the act 512 has been omitted, the treatment manager delivers one or more pacing pulses to the patient in accord with default pacing parameters stored in the data storage. In at least one example, the default pacing parameter values are each set at the maximum of each range.

In the act 802, the one or more pacing pulses may be delivered in conjunction with one or more TENS pulses executed according to a TENS routine associated with the pacing routine 800. In at least some examples, the TENS pulses are delivered between pacing pulses to distract the patient and decrease the discomfort of the pacing routine 800.

In act 804, the treatment manager receives (via the one or more electrodes) and analyzes (via the cardiac monitor) electrode signals generated from detectable characteristics of the patient's cardiac function. In act 806, the cardiac monitor determines whether delivery of the one or more pacing pulses resulted in capture or improved cardiac function. The cardiac monitor may make this determination by analyzing processed electrode data to determine whether a normal heart beat resulted from one of the one or more pacing pulses. The cardiac monitor may also make this determination by analyzing processed acoustic data from an acoustic sensor included in the medical device as disclosed in U.S. Patent Application Publication No. US2015/0005588, titled "THERAPEUTIC DEVICE INCLUDING ACOUSTIC SENSOR" and published Jan. 1, 2015, which is hereby incorporated herein by reference in its entirety. For instance, the cardiac monitor may infer capture from detection of the S1 and S2 heart sounds proximal to delivery of the pacing pulse.

In some examples of the act 806, the cardiac monitor does not infer capture has occurred until the patient's heart rate is equal to or transgresses the patient's hysteresis rate for a predetermined period (e.g., 6 seconds or 5 heartbeats). If delivery of the one or more pacing pulses did not result in capture, the treatment manager proceeds to the act 812.

In act 808, the discomfort monitor prompts for, receives, and records discomfort information and records any discomfort information acquired during execution of the pacing pulses for subsequent processing. In some examples, the discomfort information is recorded in the data storage. This discomfort information may be received as voluntary or involuntary input from the user via the user interface or may be acquired from one or more other sensors coupled to a sensor interface. Examples of discomfort information received via the user interface include utterances (e.g., words, moans, groans, crying, or other expressions) and actuation of a discomfort measuring and/or indicating device (e.g., strain gauge, button, rotary dial, elastic deformable solid). For example, the user can indicate a level of discomfort he or she feels by actuating any of one or more user interface elements as described herein. Examples of discomfort information received via other sensors (e.g., motion detection sensors, strain gauges in a garment) include movements (e.g., tensing of muscles, jerking, shuttering, flinching, changes in respiration) and lack of movement.

In some examples where the discomfort information is received as voluntary input, the discomfort monitor may prompt the user for the input by, for example, presenting a discomfort scale via the user interface. The discomfort scale may include numeric values and the user interface may request that the user rate the discomfort experienced on the numeric scale. The discomfort scale may also include graphical representations (e.g., faces) and the user interface may request that the user rate the discomfort experienced on the graphical scale. In some examples, the discomfort monitor infers the intensity of the discomfort based on the amount of pressure detected by the user interface or the amount of time a user interface element remains actuated. For example, in a manner similar to that outlined above for the baseline process, the voluntary input may be in the form of actuation of one or more user interface elements, such as a force sensor (e.g., piezoelectric, quartz, or ceramic based transducer), a push or squeeze button, a rotary spring-loaded dial, or an elastic deformable solid.

In some examples where the discomfort information is received as voluntary input, the discomfort monitor may prompt the user for a change in input where the input has not changed state for a time period greater than a value of a timeout configurable parameter of the medical device. In this way, these examples prevent involuntary input received as voluntary input from affecting the behavior of the medical device for a time period greater than the timeout.

In the act 810, the discomfort monitor determines whether the pacing pulses delivered in the previous iteration of the act 802 were tolerable to the patient. If the pacing pulses were tolerable, the treatment manager proceeds to the act 810. If the pacing pulses were not tolerable, the treatment manager proceeds to the act 808. In some examples, the discomfort monitor determines whether the pacing pulses were tolerable at least in part by quantifying discomfort information. This discomfort information quantified by the discomfort monitor may have been acquired during execution of the pacing pulses in the act 802 or may have been received as voluntary input in response to one or more prompts provided to the user via the user interface within the act 808 (i.e., after execution of the pacing pulses in act 802 is complete). In some examples, the discomfort monitor assigns a value to the discomfort parameter based on the discomfort information using one or more of the mechanisms described herein (e.g., the mechanisms described above with reference to the act 408 of FIG. 4). For instance, the discomfort monitor may store any of the following values as the value of the discomfort parameter: a value of a point on the discomfort scale selected via user input, a value calculated based on an amount of pressure exerted by the user on an element of the user interface, or a value calculated based on motion of the patient or some other involuntary reaction to the pacing pulses exhibited by the patient.

In some examples, the discomfort monitor determines whether the pacing pulses were tolerable by comparing the value of the discomfort parameter to a discomfort threshold value. This discomfort threshold value may be a configurable parameter of the medical device. In some examples, the discomfort monitor determines that the pacing pulses were tolerable where the value of the discomfort parameter maintains a predefined relationship with to the discomfort threshold value (e.g., where the value of the discomfort parameter does not transgress the discomfort threshold value). In these examples, the discomfort monitor determines that the pacing pulses were not tolerable where the value of the discomfort parameter does not maintain a predefined relationship with the discomfort threshold value (e.g. where the value of the discomfort parameter is equal to or transgresses the discomfort threshold value). It is appreciated that, depending on the specific calculations used, a discomfort threshold value may be transgressed by a value that is greater than or less than the discomfort threshold value.

In act 808, the discomfort monitor adjusts the pacing parameters. In some examples, the discomfort monitor determines the adjusted pacing parameters substantially in real time based on immediate feedback from the patient as described above with reference to FIG. 16.

In some examples, where voluntary feedback is unavailable (e.g., the patient is unable to provide dynamic feedback regarding his or her level of discomfort) the discomfort monitor determines the adjusted pacing parameters in a similar manner as outlined above with respect to the baseline process 400 by solving an optimization problem similar to the optimization problem described above with reference to described above with reference to act 412 of FIG. 4. However, the optimization problem solved within the act 812 replaces at least one of the these constraints:

15 milliamps≤$a_i$≤200 milliamps;
0.5 milliseconds≤$w_i$≤40 milliseconds;
20 pacing pulses per minute≤$r_i$≤200 pacing pulses per minute;
20 microseconds≤$p_i$≤500 microseconds;
10 percent≤$d_i$≤100 percent; and
40 microseconds≤$c_i$≤100 microseconds;
with a corresponding one of these following constraints:
$a_i \geq a_{i-1}$;
$w_i \geq w_{i-1}$;
$r_i \geq r_{i-1}$;
$p_i \geq p_{i-1}$;
$d_i \geq d_{i-1}$; and
$c_i \geq c_{i-1}$. In addition, the discomfort monitor improves any approximation of the function d(i) by incorporating the data point(s) generated in act 810.

In some examples, where the patient is not actively contributing discomfort information (e.g., the patent is unconscious), the treatment manager adjusts the pacing parameters to increase the efficacy of the pacing pulses as described above, for instance, by increasing the current by 2 milliamps. In some examples, wherein the patient is not actively contributing discomfort information, the treatment manager determines the adjusted pacing parameters by solving an optimization problem similar to the optimization problem described above with reference to described above with reference to act 412 of FIG. 4. However, the optimization problem solved within the at 812 replaces at least one of the these constraints:

15 milliamps≤$a_i$≤200 milliamps;
0.5 milliseconds≤$w_i$≤40 milliseconds;
20 pacing pulses per minute≤$r_i$≤200 pacing pulses per minute;
20 microseconds≤$p_i$≤500 microseconds;
10 percent≤$d_i$≤100 percent; and
40 microseconds≤$c_i$≤100 microseconds;
with a corresponding one of these following constraints:
$a_i \leq a_{i-1}$;
$w_i \leq w_{i-1}$;
$r_i \leq r_{i-1}$;
$p_i \leq p_{i-1}$;
$d_i \leq d_{i-1}$; and
$c_i \leq c_{i-1}$. In addition, the discomfort monitor improves any approximation of the function d(i) by incorporating the data point(s) generated in act 810.

In act 814, the treatment manager receives (via the one or more electrodes) and analyzes (via the cardiac monitor) electrode signals generated from detectable characteristics of the patient's cardiac function. During the analysis, the cardiac monitor determines whether the patient's current cardiac condition warrants further pacing. If so, the treatment manager returns to the act 802 and continues execution of the pacing routine 800. If the cardiac monitor determines that the patient's current cardiac condition does not warrant further pacing (e.g., determines whether a normal sinus rhythm has returned), the pacing routine 800 ends. In some examples, upon termination of the pacing routine 800, the treatment manager returns to the process 500 and continues to monitor the patient's physiological signals, such as the patient's ECG, temperature, pulse oxygen level, respiration, etc.

Processes in accord with the managed pacing routine 800 enable patients to control parameters of pacing routines via feedback provided to a user interface, thereby enabling patients to actively manage discomfort associated with external pacing processes.

It should be appreciated that in the various examples described above, an medical device has been described which may not only provide life-saving defibrillation or cardioversion therapy, but may also provide a wide variety of different pacing regimens. Because the medical device can monitor a patient's intrinsic cardiac activity, the patient's thoracic impedance, and other physiological characteristics of the patient, the medical device may be configured to recommend various settings to a medical professional for review and approval. The various settings that may be recommended may include a recommended base pacing rate, a recommended hysteresis rate, a recommended anti-tachyarrhythmic pacing rate, a recommended energy level (or initial energy level if capture management is used), a recommended blanking interval, and/or refractory period, and a recommended sensitivity threshold. In the case of a pacing device such as the LifeVest® cardioverter defibrillator, this initial recommendation may be performed when the patient is being fitted for and trained on the use of the medical device.

Although the ability to recommend such settings to a medical professional for their review and approval is particularly well suited to a LifeVest® cardioverter defibrillator, such functionality could also be implemented in an Automated External Defibrillator (AED) or an Advanced Life Support (ALS) type of defibrillator, such as the M Series defibrillator, R Series ALS defibrillator, R Series Plus defibrillator, or E Series defibrillator manufactured by the ZOLL Medical Corporation of Chelmsford Mass. It should be appreciated that monitoring the patient's intrinsic cardiac activity and other physiological characteristics and making recommendations to a trained medical professional for their review and approval (or possible modification) could reduce the amount of time that is spent manually configuring such devices prior to use on the patient.

Each of the processes described herein depict one particular sequence of acts in a particular embodiment. The acts included in these processes may be performed by, or using, one or more computer systems specially configured as discussed herein. Some acts are optional and, as such, may be omitted in accord with one or more embodiments. Additionally, the order of acts can be altered, or other acts can be added, without departing from the scope of the embodiments described herein.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. An external medical device comprising:
   a user interface;
   at least one therapy electrode configured to be disposed on a patient; and
   a processor operatively coupled to the at least one therapy electrode, the processor configured to
   detect a cardiac condition of the patient;
   receive, via the user interface, discomfort information descriptive of discomfort experienced by the patient;
   responsive to determining from the discomfort information that the patient is unconscious, execute at least one pacing routine, the at least one pacing routine being associated with the cardiac condition; and
   responsive to determining from the discomfort information that the patient is conscious, adjust at least one characteristic of the at least one pacing routine.

2. The external medical device of claim 1, wherein the processor is further configured to, responsive to determining from the discomfort information that the patient is unconscious, adjust the at least one characteristic of the at least one pacing routine to an upper bound of a range of values for a discomfort parameter.

3. The external medical device of claim 1, wherein the discomfort information is determined with reference to an amount of pressure exerted by the patient on an element of the user interface.

4. The external medical device of claim 1, wherein the user interface comprises at least one of a touch screen, a button, a strain gauge, a force sensor, a piezoelectric transducer, and a rotating spring-loaded dial.

5. The external medical device of claim 1, wherein the user interface comprises a force sensor configured to detect a force applied by the patient squeezing at least one surface of the force sensor.

6. The external medical device of claim 5, wherein the force sensor of the user interface is at least one of a quartz sensor, a ceramic force sensor, and a piezoelectric transducer.

7. The external medical device of claim 1, wherein the at least one characteristic of the at least one pacing routine includes at least one of an amplitude of pacing pulses, a width of the pacing pulses, a rate of the pacing pulses, a waveform of the pacing pulses, a period of the pacing pulses, a duty cycle of the pacing pulses, and a ramp time constant of the pacing pulses.

8. The external medical device of claim 1, wherein the cardiac condition comprises at least one of bradycardia and asystole.

9. The external medical device of claim 1, wherein the cardiac condition comprises at least one of tachycardia, pulseless electrical activity, and erratic heart rate.

10. The external medical device of claim 1, wherein the at least one pacing routine comprises at least one of fixed rate pacing, fixed energy pacing, adjustable rate pacing, and capture management pacing.

11. The external medical device of claim 1, wherein the processor is further configured to execute a baseline process during an initial fitting of the external medical device to the patient.

12. The external medical device of claim 11, wherein the processor is further configured to determine, during the baseline process, at least one of a range of values for a discomfort parameter corresponding to at least one pacing routine.

13. The external medical device of claim 1, further comprising a transcutaneous electrical nerve stimulation unit configured to provide background stimulation to the patient during execution of the at least one pacing routine.

* * * * *